(12) United States Patent
Love et al.

(10) Patent No.: US 7,803,823 B2
(45) Date of Patent: *Sep. 28, 2010

(54) 2-AMINO-4,5-TRISUBSTITUTED THIAZOLYL DERIVATIVES

(75) Inventors: Christopher John Love, Deurne (BE);
Guy Rosalia Eugeen Van Lommen, Berlaar (BE); Julien Georges Pierre-Olivier Doyon, Turnhout (BE); Jean-Pierre André Marc Bongartz, Turnhout (BE); Marcel Jozef Maria Van der Aa, Ravels (BE); Robert Jozef Maria Hendrickx, Beerse (BE); Peter Jacobus Johannes Antonius Buijnsters, Breda (NL); Ludwig Paul Cooymans, Beerse (BE); Nele Vandermaesen, Olmen (BE); Erwin Coesemans, Nijlen (BE); Gustaaf Maria Boeckx, Oud-Turnhout (BE)

(73) Assignee: Janssen Pharmaceutica NV (BE)

( * ) Notice: Subject to any disclaimer, the term of this patent is extended or adjusted under 35 U.S.C. 154(b) by 0 days.

This patent is subject to a terminal disclaimer.

(21) Appl. No.: 11/742,741

(22) Filed: May 1, 2007

(65) Prior Publication Data

US 2007/0203189 A1 Aug. 30, 2007

Related U.S. Application Data

(62) Division of application No. 10/486,819, filed on Feb. 11, 2004, now Pat. No. 7,232,838.

(30) Foreign Application Priority Data

Aug. 13, 2001 (EP) .................................. 01203087

(51) Int. Cl.
*A61K 31/425* (2006.01)
*C07D 277/20* (2006.01)
(52) U.S. Cl. ....................... 514/365; 514/369
(58) Field of Classification Search ................. 514/365, 514/369, 370, 385; 548/200, 202, 300.1
See application file for complete search history.

(56) References Cited

U.S. PATENT DOCUMENTS 3,459,731 A 8/1969 Gramera et al.

(Continued)

FOREIGN PATENT DOCUMENTS

DE 34062329 A1 8/1985

(Continued)

OTHER PUBLICATIONS

Patini, et al., Chem. Rev., 1996, 96, 3147-3176, especially p. 3149.*
Nogradi, M., et al., "Dimethyl-β-Cyclodextrin." *Drugs of the Future*, 1984, pp. 577-578, vol. 9, No. 8.

Ramchandra, R., et al., "Activity of Acryloyl Thiazoles, Thiazolyl Aminopyrimidines and Thiazolyl Thiopyrimidines on *Aspergillus flavus* Link, ex fries in Vitro." *Indian bot. Reptri*. 1985, pp. 144-147, vol. 2, No. 4.
Corsaro, A., et al., "A Convenient Synthesis of 2-Alkyl-and 2 Arylamino-4-Aryl-5-Cya Nothiazoles." *Heterocycles*, 1985, pp. 2645-2649, vol. 23, No. 10.

(Continued)

*Primary Examiner*—Susannah Chung

(57) ABSTRACT

This invention concerns the use of a compound of formula (I')

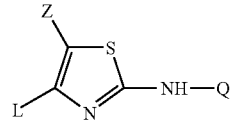

(I')

a N-oxide, a pharmaceutically acceptable addition salt, a quaternary amine and a stereochemically isomeric form thereof, wherein Z is halo; $C_{1-6}$alkyl; $C_{1-6}$alkylcarbonyl; $C_{1-6}$alkyloxycarbonyl; aminocarbonyl; $C_{1-6}$alkyl substituted with hydroxy, carboxyl, cyano, amino, amino substituted with piperidinyl, amino substituted with $C_{1-4}$alkyl substituted piperidinyl, mono- or di($C_{1-6}$alkyl)amino, aminocarbonyl, mono- or di($C_{1-6}$alkyl)aminocarbonyl, $C_{1-6}$alkyloxycarbonyl, $C_{1-6}$alkyloxy, piperidinyl, piperazinyl, morpholinyl, thiomorpholinyl; polyhalo$C_{1-4}$alkyl; cyano; amino; mono- or di($C_{1-6}$alkyl)aminocarbonyl; $C_{1-6}$alkyloxycarbonyl; $C_{1-6}$alkylcarbonyloxy; aminoS($=$O)$_2$—; mono- or di($C_{1-6}$alkyl)aminoS($=$O)$_2$; —C($=$N—R$^x$)NR$^y$R$^z$; Q is optionally substituted $C_{3-6}$cycloalkyl, phenyl, pyridyl, pyrimidinyl, pyrazinyl, pyridazinyl, benzthiazolyl, benzoxazolyl, benzimidazolyl, indazolyl, or imidazopyridyl, or Q is a radical of formula

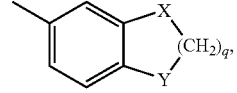

(b-1)

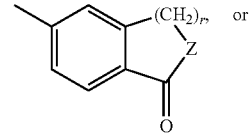

(b-2)

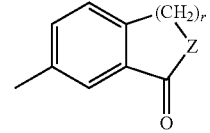

(b-3)

L is optionally substituted phenyl or an optionally substituted monocyclic 5 or 6-membered partially saturated or aromatic heterocycle or a bicyclic partially saturated or aromatic heterocycle; aryl is optionally substituted phenyl; for the manufacture of a medicament for the prevention or the treatment of inflammatory and/or auto-immune diseases mediated through TNF-α and/or IL-12.

5 Claims, No Drawings

U.S. PATENT DOCUMENTS

| | | | |
|---|---|---|---|
| 3,933,838 | A | 1/1976 | Manghisi et al. |
| 4,612,321 | A | 9/1986 | Terao et al. |
| 4,649,146 | A | 3/1987 | Takaya et al. |
| 5,000,775 | A | 3/1991 | Grabiak et al. |
| 6,403,588 | B1 * | 6/2002 | Hayakawa et al. ........... 514/249 |
| 2006/0211704 | A1 * | 9/2006 | Love et al. ............. 514/252.05 |

FOREIGN PATENT DOCUMENTS

| | | |
|---|---|---|
| EP | 154 190 A1 | 9/1985 |
| EP | 790 057 B1 | 8/1997 |
| JP | 62-67022 A | 9/1994 |
| JP | 7-149745 A | 6/1995 |
| WO | WO 97/18839 A1 | 5/1997 |
| WO | WO 99/64418 A1 | 12/1999 |
| WO | WO 02/34748 A1 | 5/2001 |
| WO | WO 01/64674 A1 | 9/2001 |

OTHER PUBLICATIONS

Badachikar, R. K. et al., "Antiinflammatory, Analgesic & Antibacterial Activities of 4-(2'-Dialkyl/diarylamino-4'-phenyl-5'-thiazolylcarbonyl)-3-arylsydnones." *Indian J. of Chem.*, 1986, pp. 444-446, vol. 25B.

Gawande, N.G., et al., Synthesis of Thiazolyl-pyrazoline & Isoxazolines from Acrylothiazoles & Their Microbial Activity. *Indian J. Chem.*, 1987, pp. 351-355, vol. 26B.

Liebscher, J. et al., "Ring Transformations via Bridged 1,3-Dicarbonyl Heteroanalogs; Part II Synthesis of 4-(w-Aminoalkyl)-thiazoles by a Novel Ring Transformation Reaction of Semicyclic Thioacylamidines with Acidic Methyl Halides." *Synthesis*, 1989, pp. 968-970, vol. 12.

Nagatomi, H., et al., "Studies on the Anti-inflammatory Activity and Ulcerogenic Adverse Effect of Thiazoles Derivatives, Expecially 2-Amino-thiazoleacetic Acid Derivatives." *Arzneim-Forsch*, 1984, pp. 599-603, vol. 5, No. 34.

Wauve, J.V., et al., "The inhibitory effect of pentamidine on the production of chemotactic cytokines by in vitro stimulated human blood cells". *Inflammatory Res.* 1996, pp. 357-363, vol. 45.

Dribi, K., et al., "Reaction of Mercaptoacetate and Halides Containing Activated Methyklenes with Thiocarbamoylimidates: A Novel Approach to the Synthesis of Aminothiazole Derivatives." *Synthesis Communications*, 1998, pp. 167-174, vol. 1, No. 28.

Richter, Monika, "Reaction behavior of selected carboxylic acid amides towards heterocumulenes, Synthesis of N-aroyl (heteroaroyl)guanidines, aroylisothioharnstoffe and 2-aminothiazoles", *Z. Chem*, 1982 (22(3), 103-4 (XP008005386).

International Search Report re: PCT/EP02/08955, dated Jul. 2, 2003.

Nath, J., et al., "Synthesis & Halogenation of Some New 2-(o-Mercaptophenyl)amino-4-Substituted-Thiazoles & Oxazoles as Pesticides", Indian J. Chem., vol. 18B(4) (1979) pp. 384-386.

Panigrahi, A., et al. "4(3'-Coumirinyl)-2-Arylamino Thiazoles and Some of Their Derivatives", Indian Chem. Soc., vol. 48(7) (1971) pp. 665-668.

Viswanathan, B., et al. "Studies on the Oxidation of Propylene on $AMoO_4$ Type Molybdates of Mn (II), CO (II), Ni (II) Cu (II) Y Zn (II)", Indian Journal of Chemistry, vol. 18A (1979) pp. 385-387.

* cited by examiner

2-AMINO-4,5-TRISUBSTITUTED THIAZOLYL DERIVATIVES

This application is a divisional of application Ser. No. 10/486,819, filed Feb. 11, 2004, now U.S. Pat. No. 7,232,838, which in turn is a 371 filing and claims the benefit of PCT/EP02/08955, filed on Aug. 9, 2002, which in turn claims the benefit of EP 01203087.0, filed on Aug. 13, 2001. The complete disclosures of the aforementioned related U.S. patent application is hereby incorporated herein by reference for all purposes.

The present invention concerns 2-amino-4,5-trisubstituted thiazolyl derivatives having proinflammatory cytokine production inhibiting properties, in particular TNF-α and/or IL-12 inhibiting properties. The invention further relates to methods for their preparation and pharmaceutical compositions comprising them. The invention also relates to the use of 2-amino-4,5-trisubstituted thiazolyl derivatives for the manufacture of a medicament for the prevention or the treatment of diseases mediated through TNF-α and/or IL-12, especially Il-12.

WO 99/64418 describes aryl-pyridyl thiazoles as TNF-α inhibitors.

WO 02/34748 concerns imidazopyridyl derivatives as anti-tumor agents.

The compounds of the present invention are distinguishable from the prior art because of their structure, pharmacological activity or potency.

The present invention relates to the use of a compound for the manufacture of a medicament for the prevention or the treatment of inflammatory and/or auto-immune diseases mediated through TNF-α and/or IL-12, wherein the compound is a compound of formula

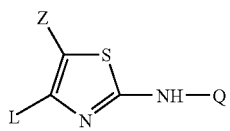

(I')

a N-oxide, a pharmaceutically acceptable addition salt, a quaternary amine and a stereochemically isomeric form thereof, wherein Z is halo; $C_{1-6}$alkyl; $C_{1-6}$alkylcarbonyl; aminocarbonyl; $C_{1-6}$alkyl substituted with hydroxy, carboxyl, cyano, amino, amino substituted with piperidinyl, amino substituted with $C_{1-4}$alkyl substituted piperidinyl, mono- or di($C_{1-6}$alkyl)amino, aminocarbonyl, mono- or di($C_{1-6}$alkyl)aminocarbonyl, $C_{1-6}$alkyloxycarbonyl, $C_{1-6}$alkyloxy, piperidinyl, piperazinyl, morpholinyl or thiomorpholinyl; polyhalo$C_{1-4}$alkyl; cyano; amino; mono- or di($C_{1-6}$alkyl)aminocarbonyl; $C_{1-6}$alkyloxycarbonyl; $C_{1-6}$alkylcarbonyloxy; amino-S(=O)$_2$—; mono- or di($C_{1-6}$alkyl)amino-S(=O)$_2$; or —C(=N—R$^x$)NR$^y$R$^z$;

R$^x$ is hydrogen, $C_{1-6}$alkyl, cyano, nitro or —S(=O)$_2$—NH$_2$;
R$^y$ is hydrogen, $C_{1-6}$alkyl, $C_{2-6}$alkenyl or $C_{2-6}$alkynyl;
R$^z$ is hydrogen or $C_{1-6}$alkyl;

Q is $C_{3-6}$cycloalkyl, phenyl, pyridyl, pyrimidinyl, pyrazinyl, pyridazinyl, benzthiazolyl, benzoxazolyl, benzimidazolyl, indazolyl, or imidazopyridyl, each of said rings optionally being substituted with up to three substituents each independently selected from halo; hydroxy; cyano; carboxyl; azido; amino; mono- or di($C_{1-6}$alkyl)amino; $C_{1-6}$alkylcarbonylamino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino or mono- or di($C_{1-4}$alkyl)amino; $C_{1-6}$alkyloxy; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo$C_{1-6}$alkyloxy; polyhalo$C_{1-6}$alkylcarbonyl; Het; $C_{1-4}$alkyl-S(=O)$_n$— or R$^1$HN—S(=O)$_n$—;
or Q is a radical of formula

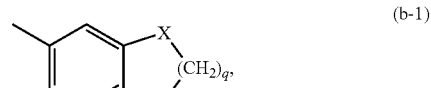

(b-1)

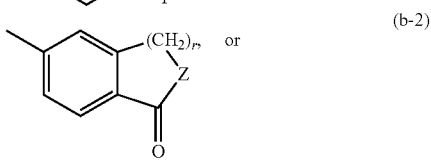

(b-2)

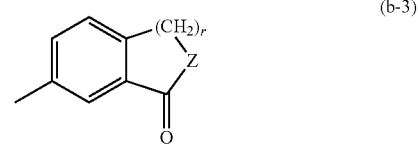

(b-3)

wherein X and Y each independently are O, NR$^3$, CH$_2$ or S, with R$^3$ being hydrogen or $C_{1-4}$alkyl;
q is an integer with value 1 to 4;
Z is O or NR$^4$ with R$^4$ being hydrogen or $C_{1-4}$alkyl;
r is an integer with value 1 to 3;
n is an integer with value 1 or 2;
R$^1$ represents hydrogen, or a radical of formula

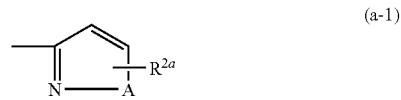

(a-1)

with A being O, S or a bivalent radical of formula —CR$^{2a}$=N— with CR$^{2a}$ attached to N of formula (a-1); and R$^{2a}$ being hydrogen, $C_{1-6}$alkyl or $C_{1-6}$alkyloxy;

L is phenyl, optionally substituted with up to 4 substituents each independently being selected from halo; hydroxy; mercapto; amino; cyano; carboxyl; mono- or di($C_{1-6}$alkyl)amino; $C_{1-6}$alkyl; $C_{1-6}$alkyl substituted with hydroxy, $C_{1-4}$alkyloxy, amino or mono- or di($C_{1-4}$alkyl)amino; polyhalo$C_{1-6}$alkyl; $C_{1-6}$alkyloxy; $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; H$_2$N—C(=O)—NH—; mono- or di($C_{1-4}$alkyl)amino-C(=O)—NH—; Het-NH—; —C(=N—R$^x$)NR$^y$R$^z$; or L is a monocyclic 5 or 6-membered partially saturated or aromatic heterocycle or a bicyclic partially saturated or aromatic heterocycle wherein each of said ring systems may optionally be substituted with up to 3 substituents, each substituent independently being selected from halo; hydroxy; mercapto; amino; cyano; carboxyl; mono- or di($C_{1-6}$alkyl)amino; $C_{1-6}$alkyl; $C_{1-6}$alkyl substituted with hydroxy, $C_{1-4}$alkyloxy, amino or mono- or di($C_{1-4}$alkyl)amino; polyhalo$C_{1-6}$alkyl; $C_{1-6}$alkyloxy; $C_{1-6}$alkylthio;

$C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; $H_2N$—C(=O)—NH—; mono- or di($C_{1-4}$alkyl)amino-C(=O)—NH—; Het-NH— or —C(=N—$R^x$)$NR^yR^z$;

Het is a monocyclic 5 or 6-membered partially saturated or aromatic heterocycle or a bicyclic partially saturated or aromatic heterocycle wherein each of said ring systems may optionally be substituted with up to 3 substitutents, each substitutent independently being selected from halo; hydroxy; amino; cyano; carboxyl; mono- or di($C_{1-6}$alkyl)amino; $C_{1-6}$alkyl; $C_{1-6}$alkyl substituted with hydroxy, $C_{1-4}$alkyloxy, amino or mono- or di($C_{1-4}$alkyl)amino; polyhalo$C_{1-6}$alkyl; $C_{1-6}$alkyloxy; $C_{1-6}$alkylthio; $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; $H_2N$—C(=O)—NH— or mono- or di($C_{1-4}$alkyl)amino-C(=O)—NH—;

aryl is phenyl, optionally substituted with up to five substitutents each independently selected from halo, hydroxy, $C_{1-6}$alkyl, polyhalo$C_{1-6}$alkyl, $C_{1-6}$alkyloxy, $C_{1-6}$alkylthio, cyano, nitro, amino or mono- or di($C_{1-6}$alkyl)amino.

The present invention also relates to a compound of formula

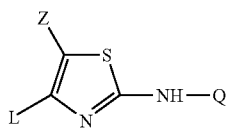

(I)

a N-oxide, a pharmaceutically acceptable addition salt, a quaternary amine and a stereochemically isomeric form thereof, wherein Z is halo; $C_{1-6}$alkyl; $C_{1-6}$alkylcarbonyl; aminocarbonyl; $C_{1-6}$alkyl substituted with hydroxy, carboxyl, cyano, amino, amino substituted with piperidinyl, amino substituted with $C_{1-4}$alkyl substituted piperidinyl, mono- or di($C_{1-6}$alkyl)amino, aminocarbonyl, mono- or di($C_{1-6}$alkyl)aminocarbonyl, $C_{1-6}$alkyloxycarbonyl, $C_{1-6}$alkyloxy, piperidinyl, piperazinyl, morpholinyl or thiomorpholinyl; polyhalo$C_{1-4}$alkyl; cyano; amino; mono- or di($C_{1-6}$alkyl)aminocarbonyl; $C_{1-6}$alkyloxycarbonyl; $C_{1-6}$alkylcarbonyloxy; amino-S(=O)$_2$—; mono- or di($C_{1-6}$alkyl)amino-S(=O)$_2$ or —C(=N—$R^x$)$NR^yR^z$;

$R^x$ is hydrogen, $C_{1-6}$alkyl, cyano, nitro or —S(=O)$_2$—$NH_2$;
$R^y$ is hydrogen, $C_{1-6}$alkyl, $C_{2-6}$alkenyl or $C_{2-6}$alkynyl;
$R^z$ is hydrogen or $C_{1-6}$alkyl;

Q is $C_{3-6}$cycloalkyl, phenyl, pyridyl, pyrimidinyl, pyrazinyl, pyridazinyl, benzthiazolyl, benzoxazolyl, benzimidazolyl, indazolyl, or imidazopyridyl, each of said rings optionally being substituted with up to three substitutents each independently selected from halo; hydroxy; cyano; carboxyl; azido; amino; mono- or di($C_{1-6}$alkyl)amino; $C_{1-6}$alkylcarbonylamino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino or mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo$C_{1-6}$alkyloxy; polyhalo$C_{1-6}$alkylcarbonyl; Het; $C_{1-4}$alkyl-S(=O)$_n$— or $R^1HN$—S(=O)$_n$—;

or
Q is a radical of formula

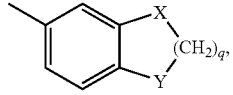

(b-1)

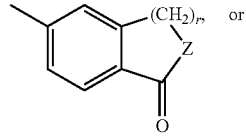

(b-2)

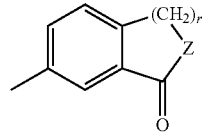

(b-3)

wherein X and Y each independently are O, $NR^3$, $CH_2$ or S, with $R^3$ being hydrogen or $C_{1-4}$alkyl;
q is an integer with value 1 to 4;
Z is O or $NR^4$ with $R^4$ being hydrogen or $C_{1-4}$alkyl;
r is an integer with value 1 to 3;
n is an integer with value 1 or 2;
$R^1$ represents hydrogen, or a radical of formula

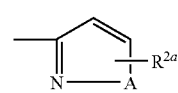

(a-1)

with A being O, S or a bivalent radical of formula —$CR^{2a}$=N— with $CR^{2a}$ attached to N of formula (a-1); and
$R^{2a}$ being hydrogen, $C_{1-6}$alkyl or $C_{1-6}$alkyloxy;

L is 3-halophenyl or 3-cyanophenyl, each optionally substituted with 1, 2 or 3 substitutents each independently being selected from halo; hydroxy; mercapto; amino; cyano; carboxyl; mono- or di($C_{1-6}$alkyl)amino; $C_{1-6}$alkyl; $C_{1-6}$alkyl substituted with hydroxy, $C_{1-4}$alkyloxy, amino or mono- or di($C_{1-4}$alkyl)amino; polyhalo$C_{1-6}$alkyl; $C_{1-6}$alkyloxy; $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; $H_2N$—C(=O)—NH—; mono- or di($C_{1-4}$alkyl)amino-C(=O)—NH—; Het-NH—; —C(=N—$R^x$)$NR^yR^z$; or L is a monocyclic 5 or 6-membered partially saturated or aromatic heterocycle or a bicyclic partially saturated or aromatic heterocycle wherein each of said ring systems may optionally be substituted with up to 3 substitutents, each substitutent independently being selected from halo; hydroxy; mercapto; amino; cyano; carboxyl; mono- or di($C_{1-6}$alkyl)amino; $C_{1-6}$alkyl; $C_{1-6}$alkyl substituted with hydroxy, $C_{1-4}$alkyloxy, amino or mono- or di($C_{1-4}$alkyl)amino; polyhalo$C_{1-6}$alkyl; $C_{1-6}$alkyloxy; $C_{1-6}$alkylthio; $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; $H_2N$—C(=O)—NH—; mono- or di($C_{1-4}$alkyl)amino-C(=O)—NH—; Het-NH— or —C(=N—$R^x$)$NR^yR^z$;

Het is a monocyclic 5 or 6-membered partially saturated or aromatic heterocycle or a bicyclic partially saturated or aromatic heterocycle wherein each of said ring systems may optionally be substituted with up to 3 substituents, each substituent independently being selected from halo; hydroxy; amino; cyano; carboxyl; mono- or di($C_{1-6}$alkyl) amino; $C_{1-6}$alkyl; $C_{1-6}$alkyl substituted with hydroxy, $C_{1-4}$alkyloxy, amino or mono- or di($C_{1-4}$alkyl)amino; polyhalo$C_{1-6}$alkyl; $C_{1-6}$alkyloxy; $C_{1-6}$alkylthio; $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; $H_2N$—C(=O)—NH— or mono- or di($C_{1-4}$alkyl)amino-C(=O)—NH—;

aryl is phenyl, optionally substituted with up to five substitutents each independently selected from halo, hydroxy, $C_{1-6}$alkyl, polyhalo$C_{1-6}$alkyl, $C_{1-6}$alkyloxy, $C_{1-6}$alkylthio, cyano, nitro, amino or mono- or di($C_{1-6}$alkyl)amino;

provided that the compound is other than 1,2-dihydro-5-[2-[(4-methoxyphenyl)amino]-5-methyl-4-thiazolyl]-6-methyl-2-oxo-3-pyridinecarbonitrile and provided that when the bicyclic aromatic heterocycle in the definition of L represents imidazopyridyl, then said imidazopyridyl is unsubstituted.

As used hereinabove or hereinafter $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl and the like; $C_{2-6}$alkenyl as a group or part of a group defines straight or branched chain hydrocarbon radicals having from 2 to 6 carbon atoms and having 1 double bond such as ethenyl, propenyl, butenyl, pentenyl, hexenyl, 3-methylbutenyl and the like; $C_{2-6}$alkynyl as a group or part of a group defines straight or branched chain hydrocarbon radicals having from 2 to 6 carbon atoms and having 1 triple bond such as ethynyl, propynyl, butynyl, pentynyl, hexynyl, 3-methylbutynyl and the like; $C_{3-6}$cycloalkyl is generic to cyclopropyl, cyclobutyl, cyclopentyl and cyclohexyl; a monocyclic or bicyclic partially saturated heterocycle represents a ring system consisting of 1 or 2 rings and comprising at least one heteroatom selected from O, N or S, and at least one double bond provided that the ring system is not an aromatic system; a monocyclic or bicyclic aromatic heterocycle represents an aromatic ring system consisting of 1 or 2 rings and comprising at least one heteroatom selected from O, N or S; the term aromatic is well known to a person skilled in the art and designates cyclically conjugated systems of 4n+2 electrons, that is with 6, 10, 14 etc. π-electrons (rule of Hückel).

The L or Q radical as described above for the compounds of formula (I) or (I') may be attached to the remainder of the molecule of formula (I) or (I') through any ring carbon or heteroatom as appropriate. For example, when Q is pyridyl, it may be 2-pyridyl, 3-pyridyl or 4-pyridyl.

Lines drawn into ring systems indicate that the bond may be attached to any suitable ring atom. When the ring system is a bicyclic ring system, the bond may be attached to any suitable ring atom of either of the two rings.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo. As used in the foregoing and hereinafter, polyhalo$C_{1-4}$alkyl or polyhalo$C_{1-6}$alkyl as a group or part of a group is defined as mono- or polyhalosubstituted $C_{1-4}$alkyl or $C_{1-6}$alkyl, for example methyl with one or more fluoro atoms, for example, difluoromethyl or trifluoromethyl, 1,1-difluoroethyl and the like. In case more than one halogen atoms are attached to an alkyl group within the definition of polyhalo$C_{1-4}$alkyl or polyhalo$C_{1-6}$alkyl, they may be the same or different.

When any variable occurs more than one time in any constituent, each definition is independent.

It will be appreciated that some of the compounds of formula (I) or (I') and their N-oxides, addition salts, quaternary amines and stereochemically isomeric forms may contain one or more centers of chirality and exist as stereochemically isomeric forms.

The term "stereochemically isomeric forms" as used hereinbefore or hereinafter defines all the possible stereoisomeric forms which the compounds of formula (I) or (I') and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) or (I') and their N-oxides, salts, solvates, quaternary amines substantially free, i.e. associated with less than 10%, preferably less than 5%, in particular less than 2% and most preferably less than 1% of the other isomers. Stereochemically isomeric forms of the compounds of formula (I) or (I') are obviously intended to be embraced within the scope of this invention.

For therapeutic use, salts of the compounds of formula (I) or (I') are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of formula (I) or (I') are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) or (I') containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like.

Conversely the salt form can be converted by treatment with acid into the free acid form.

The term addition salt as used hereinabove also comprises the solvates which the compounds of formula (I) or (I') as well as the salts thereof, are able to form. Such solvates are for example hydrates, alcoholates and the like.

The term "quaternary amine" as used hereinbefore defines the quaternary ammonium salts which the compounds of formula (I) or (I') are able to form by reaction between a basic nitrogen of a compound of formula (I) or (I') and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include for example chloro, bromo, iodo, trifluoroacetate and acetate. The counterion of choice can be made using ion exchange resin columns.

The N-oxide forms of the present compounds are meant to comprise the compounds of formula (I) wherein one or several tertiary nitrogen atoms are oxidized to the so-called N-oxide.

Some of the compounds of formula (I) or (I') may also exist in their tautomeric form. Such forms although not explicitly indicated in the above formula are intended to be included within the scope of the present invention.

Particular examples of monocyclic or bicyclic partially saturated heterocycles are pyrrolinyl, imidazolinyl, pyrazolinyl, 2,3-dihydrobenzofuranyl, 1,3-benzodioxolyl, 2,3-dihydro-1,4-benzodioxinyl, indolinyl and the like.

Particular examples of monocyclic or bicyclic aromatic heterocycles are azetyl, oxetylidenyl, pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl.

An interesting embodiment of the present invention concerns those compounds of formula (I') or (I) wherein Q is $C_{3-6}$cycloalkyl, phenyl, pyridyl, pyrimidinyl, pyrazinyl, pyridazinyl, benzthiazolyl, benzoxazolyl, benzimidazolyl, indazolyl, or imidazopyridyl, each of said rings optionally being substituted with up to three substitutents each independently selected from halo; hydroxy; cyano; carboxyl; azido; amino; mono- or di($C_{1-6}$alkyl)amino; $C_{1-6}$alkylcarbonylamino; $C_{1-6}$alkyl; $C_{2-6}$-alkenyl; $C_{2-6}$alkynyl; $C_{3-6}$cycloalkyl; $C_{1-6}$alkyl substituted with hydroxy, $C_{1-6}$alkyloxy, amino or mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo-$C_{1-6}$alkyloxy; polyhalo$C_{1-6}$alkylcarbonyl; $C_{1-4}$alkyl-S(=O)$_n$— or $R^1$HN—S(=O)$_n$—;

or

Q is a radical of formula

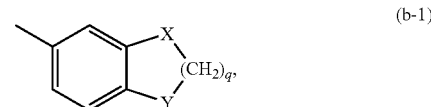

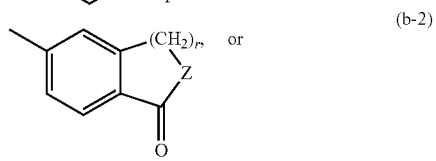

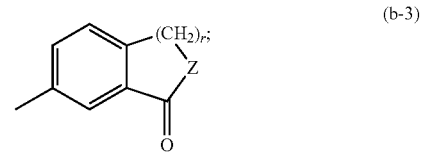

and wherein Z is halo; $C_{1-6}$alkyl; $C_{1-6}$alkylcarbonyl; aminocarbonyl; $C_{1-6}$alkyl substituted with hydroxy, carboxyl, cyano, amino, mono- or di($C_{1-6}$alkyl)amino, aminocarbonyl, mono- or di($C_{1-6}$alkyl)aminocarbonyl, $C_{1-6}$alkyloxycarbonyl, $C_{1-6}$alkyloxy, piperidinyl, piperazinyl, morpholinyl or thiomorpholinyl; polyhalo$C_{1-4}$alkyl; cyano; amino; mono- or di($C_{1-6}$alkyl)aminocarbonyl; $C_{1-6}$alkyloxycarbonyl; $C_{1-6}$alkylcarbonyloxy; amino-S(=O)$_2$—; mono- or di($C_{1-6}$alkyl)amino-S(=O)$_2$ or —C(=N—$R^x$)NR$^y$R$^z$.

Another interesting embodiment of the present invention concerns those compounds of formula (I') or (I) wherein Q is $C_{3-6}$cycloalkyl, phenyl, pyridyl, pyrimidinyl, pyrazinyl, pyridazinyl, benzthiazolyl, benzoxazolyl, benzimidazolyl, indazolyl, or imidazopyridyl, each of said rings optionally being substituted with up to three substitutents each independently selected from halo; hydroxy; cyano; carboxyl; azido; amino; mono- or di($C_{1-6}$alkyl)amino; $C_{1-6}$alkylcarbonylamino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino or mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo-$C_{1-6}$alkyloxy; polyhalo$C_{1-6}$alkylcarbonyl; Het or $C_{1-4}$alkyl-S(=O)$_n$—; or wherein Q is $C_{3-6}$cycloalkyl, phenyl, pyridyl, pyrimidinyl, pyrazinyl, pyridazinyl, benzthiazolyl, benzoxazolyl, benzimidazolyl, indazolyl, or imidazopyridyl, each of said rings optionally being substituted with up to three substitutents each independently selected from halo; hydroxy; cyano; carboxyl; azido; amino; mono- or di($C_{1-6}$alkyl)amino; $C_{1-6}$alkylcarbonylamino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo-$C_{1-6}$alkyloxy; polyhalo$C_{1-6}$alkylcarbonyl or $C_{1-4}$alkyl-S(=O)$_n$—.

Also an interesting embodiment of the present invention concerns those compounds of formula (I) or (I') wherein one or more of the following restrictions apply:

a) L is 3-halophenyl or 3-cyanophenyl, each optionally substituted with 1, 2 or 3 substitutents each independently being selected from halo; hydroxy; mercapto; amino; cyano; carboxyl; mono- or di($C_{1-6}$alkyl)amino; $C_{1-6}$alkyl; $C_{1-6}$alkyl substituted with hydroxy, $C_{1-4}$alkyloxy, amino or mono- or di($C_{1-4}$alkyl)amino; polyhalo$C_{1-6}$alkyl; $C_{1-6}$alkyloxy; $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; $H_2N$—C(=O)—NH—; mono- or di($C_{1-4}$alkyl)amino-C(=O)—NH—; Het-NH—; —C(=N—$R^x$)$NR^yR^z$; in particular L is 3-halophenyl or 3-cyanophenyl; or L is a monocyclic 5 or 6-membered partially saturated or aromatic heterocycle or a bicyclic partially saturated or aromatic heterocycle wherein each of said ring systems may optionally be substituted with up to 3 substitutents, each substitutent independently being selected from halo; hydroxy; mercapto; amino; cyano; carboxyl; mono- or di($C_{1-6}$alkyl)amino; $C_{1-6}$alkyl; $C_{1-6}$alkyl substituted with hydroxy, $C_{1-4}$alkyloxy, amino or mono- or di($C_{1-4}$alkyl)amino; polyhalo$C_{1-6}$alkyl; $C_{1-6}$alkyloxy; $C_{1-6}$alkylthio; $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; $H_2N$—C(=O)—NH—; mono- or di($C_{1-4}$alkyl)amino-C(=O)—NH—; Het-NH— or —C(=N—$R^x$)$NR^yR^z$;

b) L is a monocyclic 5 or 6-membered partially saturated or aromatic heterocycle or a bicyclic partially saturated or aromatic heterocycle wherein each of said ring systems may optionally be substituted with up to 3 substitutents, each substitutent independently being selected from halo; hydroxy; mercapto; amino; cyano; carboxyl; mono- or di($C_{1-6}$alkyl)amino; $C_{1-6}$alkyl; $C_{1-6}$alkyl substituted with hydroxy, $C_{1-4}$alkyloxy, amino or mono- or di($C_{1-4}$alkyl)amino; polyhalo$C_{1-6}$alkyl; $C_{1-6}$alkyloxy; $C_{1-6}$alkylthio; $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; $H_2N$—C(=O)—NH—; mono- or di($C_{1-4}$alkyl)amino-C(=O)—NH—, Het-NH— or —C(=N—$R^x$)$NR^yR^z$;

c) Q is phenyl, pyridyl, pyrimidinyl, pyrazinyl, pyridazinyl, benzthiazolyl, benzoxazolyl, benzimidazolyl, indazolyl, or imidazopyridyl, each of said rings optionally being substituted with up to three substitutents each independently selected from halo; hydroxy; cyano; carboxyl; azido; amino; mono- or di($C_{1-4}$alkyl)amino; $C_{1-6}$alkylcarbonylamino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino or mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo-$C_{1-6}$alkyloxy; polyhalo$C_{1-6}$alkylcarbonyl; Het or $C_{1-4}$alkyl-S(=O)$_n$—;

d) Z is halo; $C_{1-6}$alkyl; $C_{1-6}$alkylcarbonyl; $C_{1-6}$alkyloxycarbonyl; aminocarbonyl; $C_{1-6}$alkyl substituted with hydroxy, cyano, amino, amino substituted with piperidinyl, amino substituted with $C_{1-4}$alkyl substituted piperidinyl, mono- or di($C_{1-6}$alkyl)amino, aminocarbonyl, mono- or di($C_{1-6}$alkyl) aminocarbonyl, $C_{1-6}$alkyloxy, piperidinyl, piperazinyl, morpholinyl or thiomorpholinyl; polyhalo$C_{1-4}$alkyl; cyano; amino; mono- or di($C_{1-6}$alkyl)aminocarbonyl; $C_{1-6}$alkylcarbonyloxy; aminoS(=O)$_2$—; mono- or di($C_{1-6}$alkyl)aminoS(=O)$_2$ or —C(=N—$R^x$)$NR^yR^z$.

Another particular embodiment of the present invention concerns those compounds of formula (I) or (I') wherein one of the following restrictions apply:

a) L is a bicyclic partially saturated or aromatic heterocycle other than 3,4-dihydro-benzoxazin-3-one wherein each of said ring systems may optionally be substituted with up to 3 substitutents, each substitutent independently being selected from halo; hydroxy; mercapto; amino; cyano; carboxyl; mono- or di($C_{1-6}$alkyl)amino; $C_{1-6}$alkyl; $C_{1-6}$alkyl substituted with hydroxy, $C_{1-4}$alkyloxy, amino or mono- or di($C_{1-4}$alkyl)amino; polyhalo$C_{1-6}$alkyl; $C_{1-6}$alkyloxy; $C_{1-6}$alkylthio; $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; $H_2N$—C(=O)—NH—; mono- or di($C_{1-4}$alkyl)amino-C(=O)—NH— or Het-NH—;

b) L is a bicyclic aromatic heterocycle wherein each of said ring systems may optionally be substituted with up to 3 substitutents, each substitutent independently being selected from halo; hydroxy; mercapto; amino; cyano; carboxyl; mono- or di($C_{1-6}$alkyl)amino; $C_{1-6}$alkyl; $C_{1-6}$alkyl substituted with hydroxy, $C_{1-4}$alkyloxy, amino or mono- or di($C_{1-4}$alkyl)amino; polyhalo$C_{1-6}$alkyl; $C_{1-6}$alkyloxy; $C_{1-6}$alkylthio; $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; $H_2N$—C(=O)—NH—; mono- or di($C_{1-4}$alkyl)amino-C(=O)—NH— or Het-NH—;

c) L is a 6-membered partially saturated or aromatic heterocycle, optionally substituted with up to 3 substitutents, each substitutent independently being selected from halo; hydroxy; mercapto; amino; cyano; carboxyl; mono- or di($C_{1-6}$alkyl)amino; $C_{1-6}$alkyl; $C_{1-6}$alkyl substituted with hydroxy, $C_{1-4}$alkyloxy, amino or mono- or di($C_{1-4}$alkyl) amino; polyhalo$C_{1-6}$alkyl; $C_{1-6}$alkyloxy; $C_{1-6}$alkylthio; $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; $H_2N$—C(=O)—NH—; mono- or di($C_{1-4}$alkyl)amino-C(=O)—NH— or Het-NH—;

d) L is a 6-membered aromatic heterocycle, optionally substituted with up to 3 substitutents, each substitutent independently being selected from halo; hydroxy; mercapto; amino; cyano; carboxyl; mono- or di($C_{1-6}$alkyl)amino; $C_{1-6}$alkyl; $C_{1-6}$alkyl substituted with hydroxy, $C_{1-4}$alkyloxy, amino or mono- or di($C_{1-4}$alkyl)amino; polyhalo$C_{1-6}$alkyl; $C_{1-6}$alkyloxy; $C_{1-6}$alkylthio; $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; $H_2N$—C(=O)—NH—; mono- or di($C_{1-4}$alkyl) amino-C(=O)—NH— or Het-NH—;

e) L is a 5-membered partially saturated or aromatic heterocycle, optionally substituted with up to 3 substitutents, each substitutent independently being selected from halo;

hydroxy; mercapto; amino; cyano; carboxyl; mono- or di($C_{1-6}$alkyl)amino; $C_{1-6}$alkyl; $C_{1-6}$alkyl substituted with hydroxy, $C_{1-4}$alkyloxy, amino or mono- or di($C_{1-4}$alkyl) amino; polyhalo$C_{1-6}$alkyl; $C_{1-6}$alkyloxy; $C_{1-6}$alkylthio; $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; $H_2$N—C(=O)—NH—; mono- or di($C_{1-4}$alkyl)amino-C(=O)—NH— or Het-NH—;

f) L is a 5-membered aromatic heterocycle, optionally substituted with up to 3 substitutents, each substitutent independently being selected from halo; hydroxy; mercapto; amino; cyano; carboxyl; mono- or di($C_{1-6}$alkyl)amino; $C_{1-6}$alkyl; $C_{1-6}$alkyl substituted with hydroxy, $C_{1-4}$alkyloxy, amino or mono- or di($C_{1-4}$alkyl)amino; polyhalo$C_{1-6}$alkyl; $C_{1-6}$alkyloxy; $C_{1-6}$alkylthio; $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; $H_2$N—C(=O)—NH—; mono- or di($C_{1-4}$alkyl)amino-C(=O)—NH— or Het-NH—.

Also an interesting embodiment of the present invention concerns those compounds of formula (I) or (I') wherein L is optionally substituted pyridyl, more in particular optionally substituted 3-pyridyl, most in particular unsubstituted 3-pyridyl.

Another interesting embodiment of the present invention concerns those compounds of formula (I) or (I') wherein Z is halo; $C_{1-6}$alkyl; $C_{1-6}$alkylcarbonyl; aminocarbonyl; $C_{1-6}$alkyl substituted with hydroxy, cyano, amino, amino substituted with piperidinyl, amino substituted with $C_{1-4}$alkyl substituted piperidinyl, mono- or di($C_{1-6}$alkyl)amino, aminocarbonyl, mono- or di($C_{1-6}$alkyl)aminocarbonyl, $C_{1-6}$alkyloxycarbonyl, $C_{1-6}$alkyloxy, piperidinyl, piperazinyl, morpholinyl or thiomorpholinyl; polyhalo$C_{1-4}$alkyl; cyano; amino; mono- or di($C_{1-6}$alkyl)aminocarbonyl; $C_{1-6}$alkyloxycarbonyl; $C_{1-6}$alkylcarbonyloxy; amino-S(=O)$_2$—; mono- or di($C_{1-6}$alkyl)amino-S(=O)$_2$; or —C(=N—$R^x$)N$R^y R^z$.

Another interesting embodiment of the present invention concerns those compounds of formula (I) or (I') wherein Z is halo, in particular fluoro; $C_{1-6}$alkyl, in particular methyl; $C_{1-6}$alkyl substituted with amino, in particular —CH$_2$—NH$_2$; $C_{1-6}$alkyl substituted with hydroxy, in particular —CH(OH)CH$_3$; $C_{1-6}$alkyl substituted with amino which is substituted with piperidinyl, in particular 4-piperidinylaminomethyl; $C_{1-6}$alkyl substituted with amino which is substituted with $C_{1-4}$alkyl substituted piperidinyl, in particular 1-methyl-4-piperidinylaminomethyl. A further interesting embodiment of the present invention concerns those compounds of formula (I) or (I') wherein Z is fluoro, methyl or —CH(OH)CH$_3$.

A further interesting embodiment of the present invention concerns those compounds of formula (I) or (I') wherein Z is fluoro, methyl or —CH(OH)CH$_3$ and L is a 5- or 6-membered partially saturated or aromatic heterocycle, optionally substituted with up to 3 substitutents, each substitutent independently being selected from halo; hydroxy; amino; cyano; carboxyl; mono- or di($C_{1-6}$alkyl)amino; $C_{1-6}$alkyl; $C_{1-6}$alkyl substituted with hydroxy, $C_{1-4}$alkyloxy, amino or mono- or di($C_{1-4}$alkyl)amino; polyhalo$C_{1-6}$alkyl; $C_{1-6}$alkyloxy; $C_{1-6}$alkylthio; $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; $H_2$N—C(=O)—NH—; mono- or di($C_{1-4}$alkyl)amino-C(=O)—NH— or Het-NH—.

A further interesting embodiment of the present invention concerns those compounds of formula (I) or (I') wherein Q is benzthiazolyl; pyridyl substituted with halo or $C_{1-6}$alkyl; phenyl or phenyl substituted with one, two or three substitutents selected from halo, $C_{1-6}$alkyl, polyhalo$C_{1-6}$alkyl, $C_{1-6}$alkyloxycarbonyl, hydroxy, $C_{1-6}$alkyloxy, $C_{1-6}$alkylthio, 1-methyl-2-imidazolyl; Z is halo; cyano; $C_{1-6}$alkylcarbonyl; aminocarbonyl; $C_{1-6}$alkyloxycarbonyl; $C_{1-6}$alkyl; $C_{1-6}$alkyl substituted with hydroxy, $C_{1-6}$alkyloxy, amino, mono- or di($C_{1-6}$alkyl)amino, piperidinylamino, 1-methyl-4-piperidinylamino or morpholinyl; L is pyridyl; pyridyl substituted with amino; 3-halophenyl; imidazopyridyl; imidazothiazolyl; pyrimidinyl; furanyl.

Still a further interesting embodiment of the present invention concerns those compounds of formula (I) or (I') wherein Q is phenyl, 3-trifluoromethyl-phenyl, 3-trifluoromethyl-4-fluoro-phenyl, 4-trifluoromethyl-phenyl, 3-bromo-phenyl, 4-bromo-phenyl, 4-fluoro-phenyl, 3-chloro-phenyl, 4-chloro-phenyl, 3-methyl-phenyl, 3-hydroxy-phenyl, 4-hydroxy-phenyl, 3-methoxy-phenyl, 4-methoxy-phenyl, 3,4-dimethoxy-phenyl, 3,4,5-trimethoxy-phenyl, 3-methylthio-phenyl, 4-methyl-phenyl, 2,3-dichloro-phenyl, 3-methyl-4-fluoro-phenyl, 3-ethyloxycarbonyl-phenyl, 4-ethyloxycarbonyl-pheny, 6-benzothiazolyl, 6-chloro-pyrid-2-yl, 6-methyl-pyrid-2-yl, 5-chloro-pyrid-3-yl, 3-trifluoromethyl-4-methoxy-phenyl; Z is bromo, chloro, fluoro, acetyl, aminocarbonyl, ethyloxycarbonyl, morpholinylethyl, morpholinylmethyl, di(methyl)aminoethyl, di(methyl)aminomethyl, ethylaminomethyl, 4-piperidinylaminomethyl, 1-methyl-4-piperidinylaminomethyl, —CH(OH)CH$_3$, aminomethyl, hydroxymethyl, methoxymethyl, cyano, methyloxycarbonyl, methyl; L is 2-amino-5-pyridyl, 3-fluoro-phenyl, 3-pyridyl, 4-pyridyl, 3-imidazopyridyl, imidazothiazol-5-yl, 5-pyrimidinyl, 5-fluoro-pyrid-3-yl, 3-furanyl.

Also an interesting embodiment of the present invention concerns those compounds of formula (I) or (I') wherein Q is phenyl, 3-trifluoromethyl-phenyl, 3-trifluoromethyl-4-fluoro-phenyl, 4-trifluoromethyl-phenyl, 3-bromo-phenyl, 4-bromo-phenyl, 4-fluoro-phenyl, 3-chloro-phenyl, 4-chloro-phenyl, 3-methyl-phenyl, 4-methoxy-phenyl, 3-methylthio-phenyl, 4-methyl-phenyl, 2,3-dichloro-phenyl, 3-methyl-4-fluoro-phenyl, 3-ethyloxycarbonyl-phenyl, 4-ethyloxycarbonyl-phenyl, 6-benzothiazolyl, 2-chloro-pyrid-5-yl, 2-methyl-pyrid-5-yl, 5-chloro-pyrid-3-yl; Z is fluoro, 4-piperidinylaminomethyl, 1-methyl-4-piperidinylaminomethyl, morpholinylmethyl, —CH(OH)CH$_3$, aminomethyl, hydroxymethyl, methyl; L is 2-amino-5-pyridyl, 3-fluoro-phenyl, 3-pyridyl, 5-fluoro-pyrid-3-yl, 3-furanyl, imidazothiazol-5-yl.

Preferred compounds of formula (I) or (I') are compounds 1, 4 and 14 (see Table 1).

In general, compounds of formula (I) wherein Z is halo, said compounds being represented by formula (I-a), can be prepared by reacting an intermediate of formula (II) with an halo-introducing agent of formula halo-R (III) wherein R represents the remaining of the halo-introducing agent, in the presence of a suitable solvent, such as for example N,N-dimethylformamide, optionally in the presence of a suitable base, such as for example 2,6-lutidine. Suitable halo-introducing agents are for example 1-chloro-pyrrolidinedione, 1-bromo-pyrrolidinedione or Selectfluor® (1-(chloromethyl)-4-fluoro-1,4-diazoniabicyclo[2.2.2]octane, bis[tetrafluoroborate(1-)]).

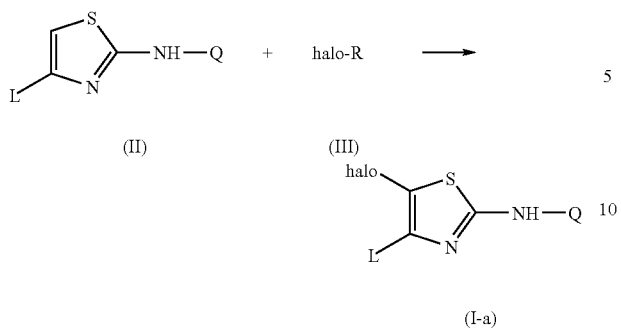

(I-a)

Compounds of formula (I) wherein Z is fluoro, said compounds being represented by formula (I-a-1), can be prepared by reacting an intermediate of formula (IV) wherein $W_1$ represents a suitable leaving group, such as for example chloro, with an intermediate of formula (V) in the presence of a suitable fluoro-introducing agent, such as for example Selectfluor®, and in the presence of a suitable solvent, such as for example N,N-dimethylformamide or an alcohol, e.g. ethanol and the like.

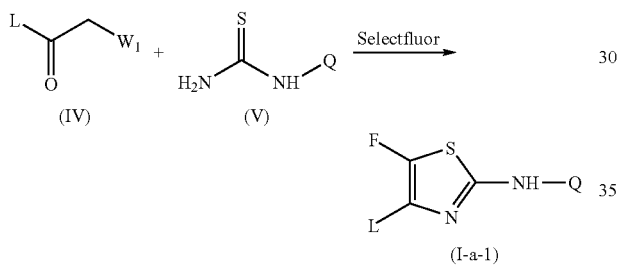

(I-a-1)

Alternatively, compounds of formula (I-a-1) can also be prepared by reacting an intermediate of formula (XX) with an intermediate of formula (V) in the presence of a suitable solvent, such as for example tetrahydrofuran.

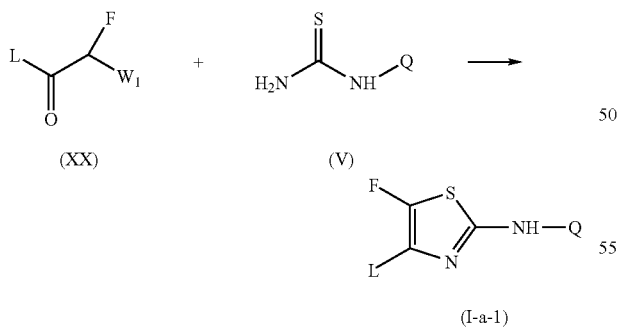

(I-a-1)

Compounds of formula (I) wherein Z is $C_{1-6}$alkyloxycarbonyl or $C_{1-6}$alkylcarbonyl, said Z being represented by $Z_a$, and said compounds being represented by formula (I-b), can be prepared by reacting an intermediate of formula (VI) with an intermediate of formula (V) in the presence of phenyl N,N,N-trimethylammonium trihalide, e.g. phenyl N,N,N-trimethylammonium tribromide, or benzyltrimethylammonium dichloroiodate and the like, and a suitable solvent, such as for example tetrahydrofuran or an alcohol, e.g. methanol, ethanol and the like.

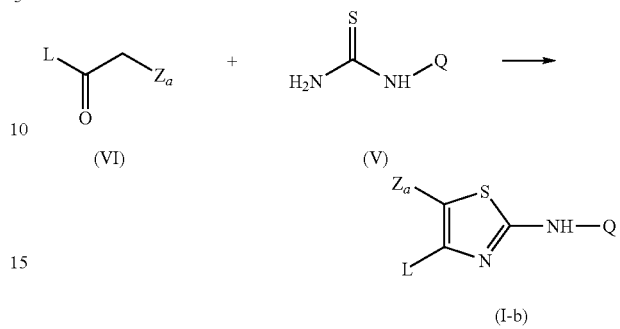

(I-b)

Compounds of formula (I) wherein Z is $C_{1-6}$alkyl or cyano, said Z being represented by $Z_b$, and said compounds being represented by formula (I-c), can be prepared by reacting an intermediate of formula (VII) wherein $W_2$ represents a suitable leaving group, such as for example halo, e.g. bromo, with an intermediate of formula (V) in the presence of a suitable solvent, such as for example an alcohol, e.g. ethanol and the like.

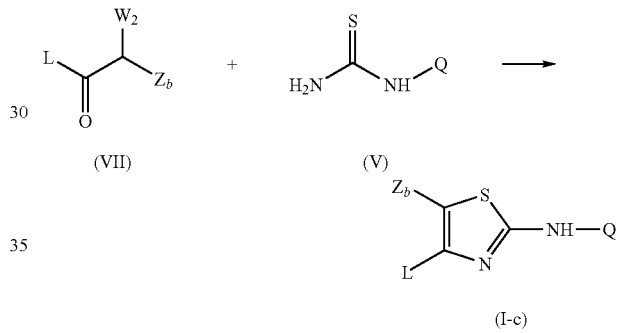

(I-c)

Compounds of formula (I-c) can also be prepared by reacting an intermediate of formula (VII') with an intermediate of formula (V) in the presence of $Br_2$ or phenyl trimethyl ammonium tribromide and a suitable solvent, such as for example methylene chloride, tetrahydrofuran and an alcohol, e.g. ethanol.

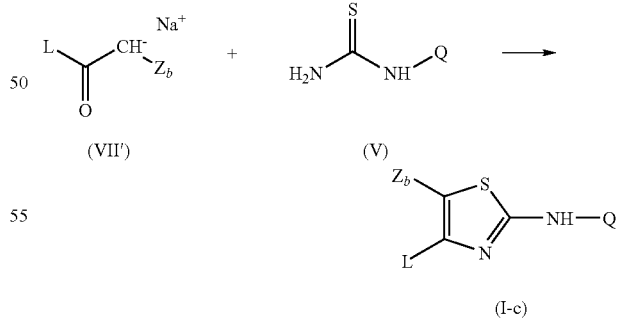

(I-c)

Compounds of formula (I) wherein Z is $C_{1-6}$alkyl substituted with amino, mono- or di($C_{1-6}$alkyl)amino, piperidinyl, piperazinyl, morpholinyl, thiomorpholinyl, said Z being represented by Z, —$C_{1-6}$alkyl, and said compounds being represented by formula (I-d), can be prepared by reacting an intermediate of formula (VIII) wherein $W_3$ represents a suitable leaving group, such as for example halo, e.g. chloro, with an intermediate of formula (IX) in the presence of a suitable base, such as for example NaHCO$_3$, and a suitable solvent, such as for example acetonitrile.

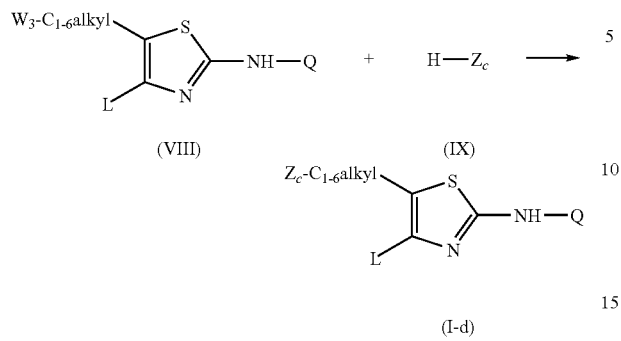

(I-d)

Compounds of formula (I) wherein Z represents CH$_2$ substituted with piperidinyl, piperazinyl, morpholinyl or thiomorpholinyl, said Z being represented by formula CH$_2$—Z$_d$ and said compounds being represented by formula (I-e), can be prepared by reacting an intermediate of formula (XVII) with an intermediate of formula (XVIII) in the presence of H$_2$, a suitable catalyst, such as for example Pt/C, and a suitable solvent, such as for example an alcohol, e.g. methanol.

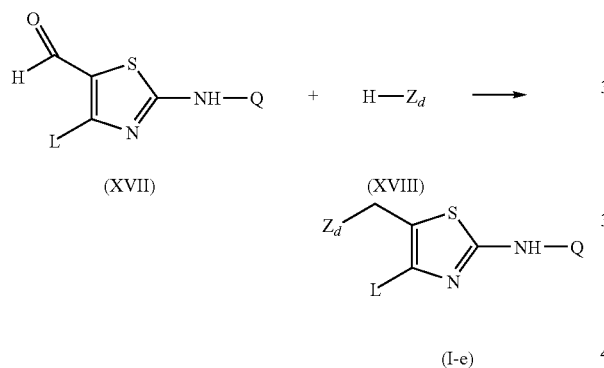

(I-e)

Compounds of formula (I) wherein Z represents C$_{1-6}$alkyl substituted with amino, which is substituted with 4-piperidinyl, said compounds being represented by formula (I-f), can be prepared by deprotecting an intermediate of formula (XIX) wherein P represents a suitable protecting group, such as for example C$_{1-6}$alkyloxycarbonyl or benzyloxycarbonyl, in the presence of a suitable acid, such as for example hydrochloric acid and the like.

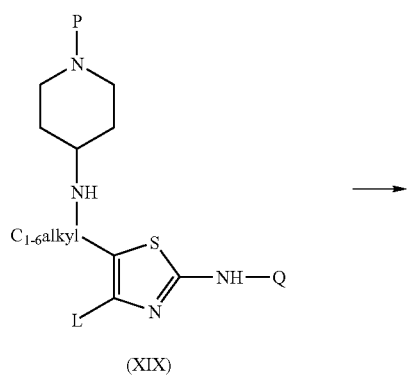

(XIX)

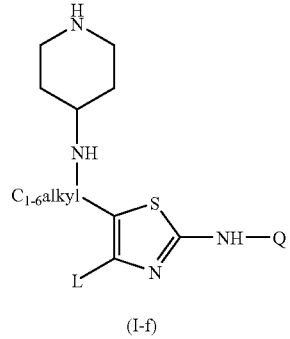

(I-f)

The use of protecting groups is fully described in 'Protective Groups in Organic Chemistry', edited by J W F McOmie, Plenum Press (1973), and 'Protective Groups in Organic Synthesis' 2$^{nd}$ edition, T W Greene & P G M Wutz, Wiley Interscience (1991). Compounds of formula (I) may be converted into each other following art-known functional group transformation reactions, comprising those described hereinafter.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein L is substituted with amino may be converted into a compound of formula (I) wherein L is substituted with C$_{1-6}$alkylcarbonylamino by reaction with a C$_{1-6}$alkylcarbonyl chloride in a suitable solvent, such as for example pyridine.

Compounds of formula (I) wherein Q is substituted with cyano may be converted into a compound of formula (I), wherein Q is substituted with carboxyl by reaction with a suitable acid, such as concentrated hydrochloric acid, in the presence of a suitable reaction-inert solvent, e.g. water.

Compounds of formula (I), wherein L is substituted with C$_{1-6}$alkyl-C(=O)—NH—, may be converted into a compound of formula (I), wherein L is substituted with amino, by reaction with a suitable acid, such as for example hydrobromic acid and the like, in the presence of a suitable solvent, such as water.

Compounds of formula (I) wherein Z is cyano may be converted into a compound of formula (I) wherein Z is aminocarbonyl by reaction in a mixture of H$_2$SO$_4$/H$_2$O.

Compounds of formula (I) wherein Z is cyano may also be converted into a compound of formula (I) wherein Z is —CH$_2$—NH$_2$ by reaction with a suitable reducing agent, such as for example H$_2$, in the presence of a suitable catalyst, such as for example Raney Nickel, and a suitable solvent, such as for example tetrahydrofuran, NH$_3$, alcohol, e.g. CH$_3$OH.

Compounds of formula (I) wherein Z is $C_{1-6}$alkyloxycarbonyl may be converted into a compound of formula (I) wherein Z is —$CH_2$—OH in the presence of a suitable reducing agent, such as for example $LiAlH_4$, and a suitable solvent, such as for example tetrahydrofuran.

Compounds of formula (I) wherein Z is $C_{1-6}$alkylcarbonyl can be converted into a compound of formula (I) wherein Z is $C_{1-5}$alkyl-CHOH— in the presence of a suitable reducing agent, such as for example $NaBH_4$ or $LiAlH_4$, and a suitable solvent, such as for example tetrahydrofuran or diethyl ether.

Compounds of formula (I) wherein Z is $C_{1-6}$alkyl substituted with amino, can be converted into a compound of formula (I) wherein Z is $C_{1-6}$alkyl substituted with amino which is substituted with piperidinyl or $C_{1-4}$alkyl substituted piperidinyl, by reaction with piperidine or $C_{1-4}$alkyl substituted piperidine in the presence of $H_2$, a suitable catalyst, such as for example palladium on charcoal, a suitable catalyst poison, such as for example a thiophene solution, and a suitable solvent, such as for example an alcohol, e.g. methanol and the like.

Compounds of formula (I) wherein Z is $C_{1-6}$alkyl substituted with amino, can also be converted into a compound of formula (I) wherein Z is $C_{1-6}$alkyl substituted with dimethylamino, by reaction with paraform in the presence of $H_2$, a suitable catalyst, such as for example palladium on charcoal, a suitable catalyst poison, such as for example a thiophene solution, and a suitable solvent, such as for example an alcohol, e.g. methanol and the like.

In the following paragraphs, there are described several methods of preparing the intermediates in the foregoing preparations. A number of intermediates and starting materials are commercially available or are known compounds which may be prepared according to conventional reaction procedures generally known in the art.

Intermediates of formula (II) can be prepared by reacting an intermediate of formula (IV) with an intermediate of formula (V) in the presence of a suitable solvent, such as for example an alcohol, e.g. ethanol.

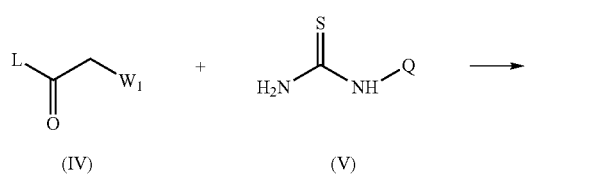

Intermediates of formula (II) can also be prepared by reacting an intermediate of formula (X) with an intermediate of formula (V) in the presence of phenyl N,N,N-trimethylammonium trihalide, e.g. phenyl N,N,N-trimethylammonium tribromide, or benzyl N,N,N-trimethylammonium dichloroiodate and the like, and a suitable solvent, such as for example tetrahydrofuran.

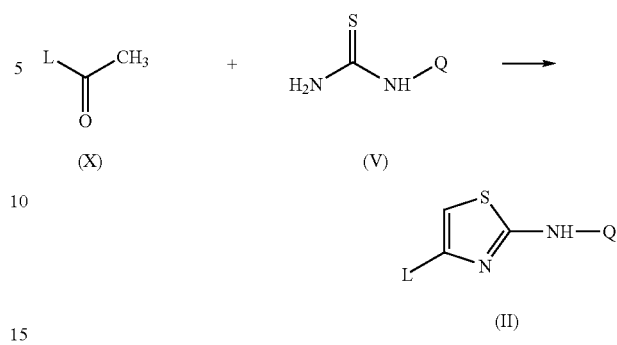

Intermediates of formula (IV) can be prepared by reacting L with an intermediate of formula (XI) wherein $W_1$ is as defined hereinabove, in the presence $C(=S)_2$ and $AlCl_3$.

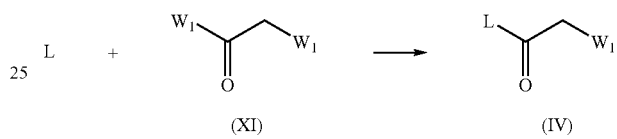

Intermediates of formula (IV) wherein $W_1$ is bromo, said intermediates being represented by formula (IV-a) can also be prepared by reacting an intermediate of formula (X) with N,N,N-trimethylbenzenaminium tribromide in the presence of a suitable solvent, such as for example tetrahydrofuran and an alcohol, e.g. methanol.

Intermediates of formula (V) can be prepared by reacting an intermediate of formula (XII) with a suitable base, such as for example sodium hydroxide, in the presence of a suitable solvent, such as for example an alcohol, e.g. ethanol.

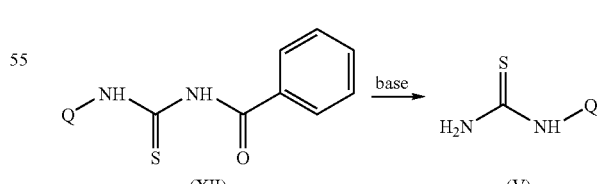

Intermediates of formula (V) can also be prepared by reacting an intermediate of formula (XIII) with benzoyl isothiocyanate in the presence of a suitable base, such as for example sodium hydroxide, and a suitable solvent, such as for example tetrahydrofuran, or an alcohol, such as for example ethanol.

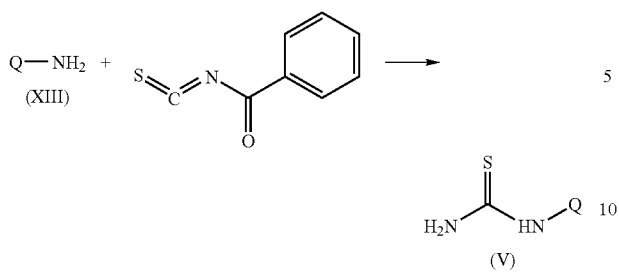

Intermediates of formula (XII) can be prepared by reacting an intermediate of formula (XIII) with benzoyl isothiocyanate in the presence of a suitable solvent, such as for example tetrahydrofuran.

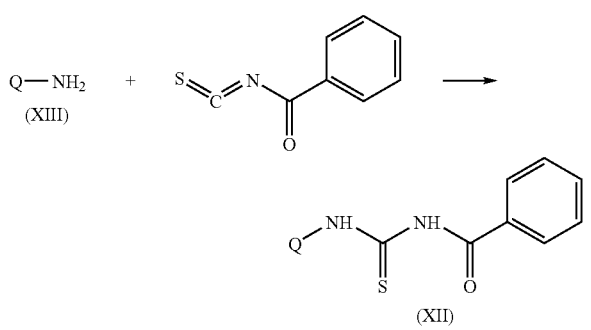

Intermediates of formula (VII) wherein $Z_b$ represents $C_{1-6}$alkyl, said intermediates being represented by formula (VII-a) can be prepared by reacting an intermediate of formula (X') with a leaving group-introducing agent of formula (XIV), such as for example $Br_2$, wherein R' represents the remaining part of the leaving group introducing agent, in the presence of a suitable acid, such as acetic acid or hydrobromic acid in water.

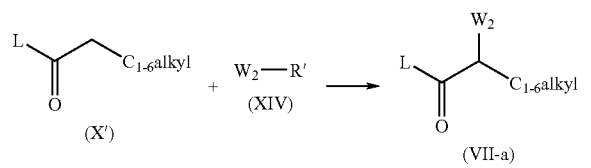

Intermediates of formula (VII) wherein $Z_b$ represents cyano, said intermediates being represented by formula (VII-b), can be prepared by reacting an intermediate of formula (VII') wherein $Z_b$ represents cyano, said intermediates being represented by formula (VII'-a) with an intermediate of formula (XIV) in the presence of a suitable solvent, such as for example methylene chloride.

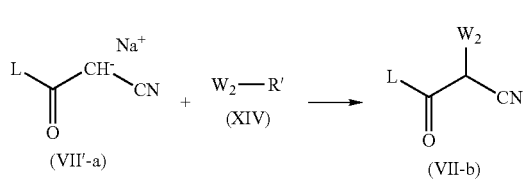

Intermediates of formula (X') can be prepared by reacting L with an intermediate of formula (XV) wherein $W_1$ is defined as hereinabove, in the presence of $AlCl_3$ and a suitable solvent, such as for example methylene chloride.

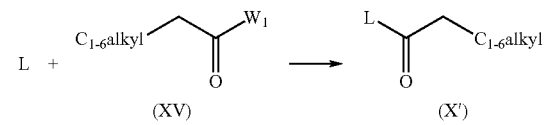

Intermediates of formula (VIII) can be prepared by reacting an intermediate of formula (XVI) wherein $W_2$ and $W_3$ are as defined hereinabove, with an intermediate of formula (V) in the presence of a suitable solvent, such as for example an alcohol, e.g. methanol.

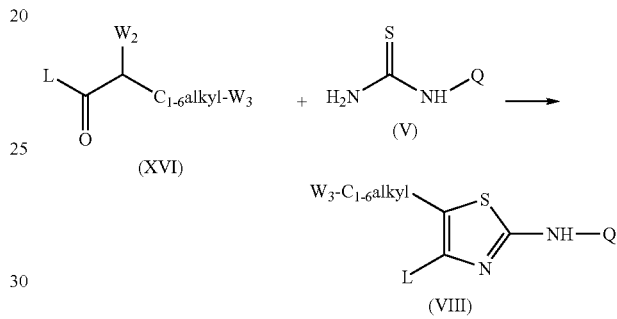

Intermediates of formula (XVI) wherein $W_2$ represents bromo, said intermediates being represented by formula (XVI-a), can be prepared by reacting an intermediate of formula (XXI) with $Br_2$ in the presence of a suitable acid, such as for example acetic acid and the like.

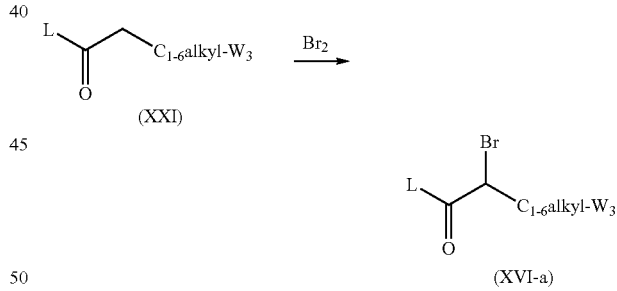

Intermediates of formula (XXI) wherein $W_3$ represents chloro and $C_{1-6}$alkyl represents —$(CH_2)_2$—, said intermediates being represented by formula (XXI-a), can be prepared by reacting an intermediate of formula (XXII) with HCl.

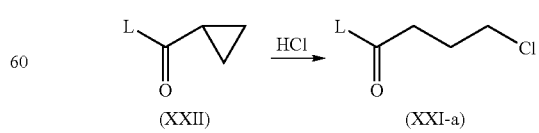

Intermediates of formula (XVII) can be prepared by reacting a compound of formula (I-a) with nBuLi in the presence of N,N-dimethylformamide and tetrahydrofuran.

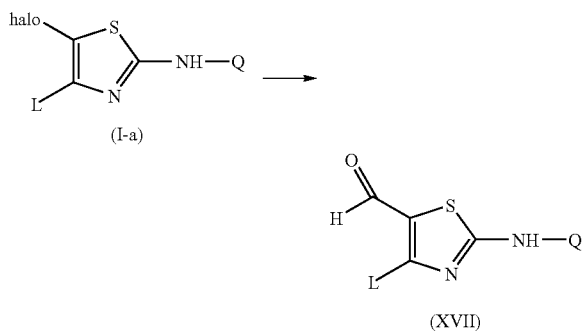

Intermediates of formula (XIX) can be prepared by reacting a compound of formula (I-d) wherein Z represents $C_{1-6}$alkylNH$_2$, said compound being represented by formula (I-d-1), with an intermediate of formula (XXIII) in the presence of H$_2$, a suitable catalyst such as for example palladium on charcoal, a suitable catalyst poison, such as for example a thiophene solution, and a suitable solvent, such as for example an alcohol, e.g. methanol and the like.

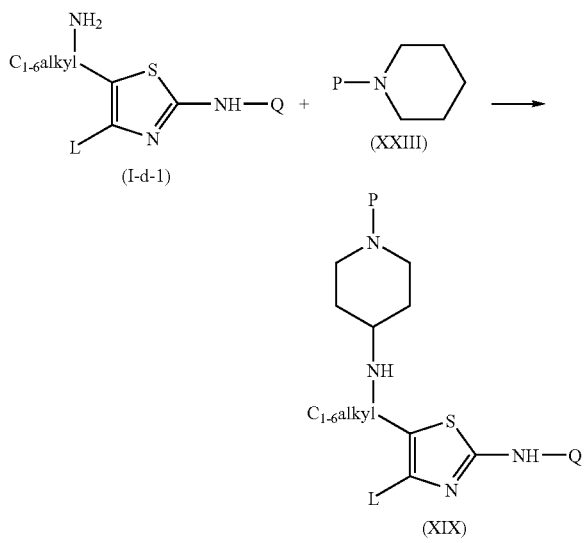

The compounds of the present invention show cytokine production modulating activity, in particular cytokine production inhibitory activity, more in particular proinflammatory cytokine production inhibitory activity. A cytokine is any secreted polypeptide that affects the function of other cells by modulating interactions between cells in the immune or inflammatory response. Examples of cytokines include Interleukin-1 (IL-1) up to Interleukin-23 (IL-23), Tumor Necrosis Factor-alpha (TNF-α), Tumor Necrosis Factor-beta (TNF-β). The present compounds also show inhibitory activity on the production of chemotacetic cytokines or chemokines responsible for trafficking and activation of leucocytes. A chemokine production inhibited by the compounds of formula (I) or (I') is MCP-1 production (Monocyte Chemotacetic Protein 1).

The cytokine production specifically inhibited by the compounds of formula (I) or (I') is TNF-α and/or Interleukin-12 (IL-12) production.

TNF-α is primarily produced by monocytes, macrophages, T and B lymphocytes, neutrophils, mast cells, tumour cells, fibroblasts, keratinocytes, astrocytes, microglial cells, smooth muscle cells and others. This proinflammatory cytokine is established at the pinnacle of proinflammatory cascades; it exerts a key role in the cytokine network with regard to the pathogenesis of many infectious, inflammatory and autoimmune diseases. Excessive or unregulated TNF-α production is implicated in mediating or exacerbating a number of diseases including rheumatoid arthritis, rheumatoid spondylitis, spondyloarthropathies, systemic lupus erythematosus, osteoarthritis, gouty arthritis, juvenile arthritis and other arthritic conditions, polychondritis, sclerodoma, Wegener granulamatosis, dermatomyositis, Steven-Johnson syndrome, idiopathic sprue, endocrine opthalmopathy, Grave's disease, alveolitis, chronic hypersensitivity pneumonitis, primary billiary cirrhosis, uveitis, keratoconjunctivitis sicca and vernal keratoconjunctivitis, allergic rhinitis, pemphigus, eosinophilia, Loffler's syndrome, eosinophilic pneumonia, parasitic infestation, bronchopulmonary aspergillosis, polyarteritis nodosa, eosinophilic granuloma, eosinophil-related disorders affecting the airways occasioned by drug-reaction, sepsis, septic shock, endotoxic shock, gram negative sepsis, toxic shock syndrome, cerebral malaria, adult respiratory distress syndrome, bronchitis (acute, arachidic, catarrhal, chronic, croupus, phthinoid bronchitis), chronic obstructive airway or pulmonary disease, pulmonary fibrosis, pneumoconiosis (aluminosis, anthracosis, asbestosis, chalicocis, ptilosis, siderosis, silicosis, tobaccosis, byssionosis), tuberculosis, silicosis, exacerbation of airways hyperreactivity to other drug therapy (e.g. aspirin or β-agonist therapy), pulmonary sarcoidosis, bone resorption diseases, meningitis, reperfusion injury, graft versus host reaction, allograft rejections, transplant rejections, fever and myalgias due to infection, such as influenza, cachexia (consequential to, e.g. bacterial, viral or parasitic, infection or to deprivation or deterioration of humoral or other organic function, or secondary to malignancy; malarial and vermal cachexia; cachexia resulting from dysfunction of the pituitary, thyroid or thymus glands as well as uremic cachexia; cachexia secondary to acquired immune deficiency syndrome (AIDS)), AIDS, ARC (AIDS related complex), diabetes, cancer, angiogenesis, lymphoma, Kawasaki syndrome, Behçet's syndrome, aphthous ulceration, skin-related disorders such as psoriasis, eczema, burns, dermatitis, keloid formation, scar tissue formation, erythema nodosum leprosum, Crohn's disease, ulcerative colitis, inflammatory bowel disease, irritable bowel syndrome, pyresis, asthma (intrinsic, extrinsic, allergic, non-atopic, exercise induced and occupational and bacterial infection induced asthma), wheezy infant syndrome, multiple sclerosis, Parkinson's disease, pancreatitis, cardiac disease, congestive heart failure, myocardial infarction, acute liver failure, glomerulonephritis, therapy-associated syndromes comprising Jarisch-Herxheimer reaction, and syndromes associated with IL-2 infusion, anti-CD3 antibody infusion, hemodialysis, yellow fever vaccination. TNF-α has also been shown to activate HIV (Human Immune deficiency Virus) replication in monocytes and/or macrophages. Therefore, inhibition of TNF-α production or activity aids in limiting HIV progression. TNF-α also plays a role in other viral infections, such as Hepatitis C, CMV (cytomegalovirus), influenza and herpes virus infections, including herpes simplex virus type-1, herpes simplex virus type-2, varicella-zoster virus, Epstein-Barr virus, human herpes virus-6, -7 and -8, pseudorabies and rhinotracheitis.

IL-12 is produced primarily by monocytes, macrophages and dendritic cells in response to bacteria, bacterial products (lipopolysaccharide) and immune signals. The production of IL-12 is regulated by other cytokines and endogenous mediators produced during inflammatory and immunological responses. IL-12 plays a central role in the immune system. Evidence obtained from animal models and human diseases suggests that inappropriate and protracted production of IL-12 and the ability of IL-12 to induce the generation of T helper 1 cell type responses may be instrumental in the development and maintenance of chronic inflammatory diseases, such as rheumatoid arthritis, collagen induced arthritis, allergic encephalitis, colitis, inflammatory bowel disease, Crohn's disease and multiple sclerosis, and in the triggering of autoimmune disorders, such as diabetes, or graft versus host diseases, shock or musculoskeletal and connective tissue diseases. The adverse effects also include anemia (haemolytic, aplastic, pure red cell, idiopatic thrombocytopenia), neutropenia, lymphopenia, hepatosplenomegaly with mononuclear cell infiltration and pulmonary edema with interstitial cell infiltrates. Excessive IL-12 production may accelerate the inflammatory progress of a disease, or the onset of the disease, such as rheumatoid arthritis, or it may also augment the disease severity.

Inhibition of TNF-α and/or IL-12 production by the compounds of formula (I) or (I') might offer an interesting, potentially less toxic alternative to non-specific immunosuppression (e.g. corticosteroids) in the treatment of chronic inflammatory and autoimmune diseases. The combined modulation of TNF-α and IL-12 production may ameliorate the treated disease to a greater extent than mono-therapy. The therapeutic effect of combining the suppression of both the immune and the inflammatory arm of a disease may provide additional clinical benefits. The present compounds are also indicated for use as co-therapeutic agents for use in conjunction with immunosuppressive and/or anti-inflammatory drugs, e.g. as potentiators of the therapeutic activity of said drugs, to reduce required dosaging or thus also potential side effects of said drugs. Immunosuppressive and/or anti-inflammatory drugs include for example cyclopeptide, cyclopeptolide or macrolide immunosuppressive or anti-inflammatory drugs, such as drugs belonging to the cyclosporin class, e.g. cyclosporine A or G, tacrolimus substances, ascomycin, rapamycin, glucocorticosteroid drugs, e.g. budesonide, beclamethasone, fluticasone, mometasone.

The compounds of formula (I) or (I') are useful in preventing or treating cytokine mediated diseases, and as such, inhibit, suppress or antagonize the production or activity of proinflammatory cytokines, such as TNF-α and/or IL-12, especially IL-12.

Disorders mediated through TNF-α and/or IL-12 refers to any and all disorders and disease states in which TNF-α and/or IL-12 play a role, either by the cytokine itself, or by the cytokine causing another cytokine, such as for example IL-1 or IL-6, or a certain mediator to be released.

Due to their cytokine production inhibitory activity, in particular their proinflammatory cytokine production inhibitory activity, more in particular their TNF-α and/or IL-12 inhibitory activity, even more in particular their IL-12 inhibitory activity, the compounds of formula (I), their N-oxides, pharmaceutically acceptable addition salts, quaternary amines and stereochemically isomeric forms are useful in the treatment or prevention of diseases or conditions mediated through cytokines, in particular diseases or conditions related to excessive or unregulated production of proinflammatory cytokines, such as TNF-α and/or IL-12, comprising inflammatory diseases or auto-immune diseases. Diseases or conditions related to an excessive or unregulated production of proinflammatory cytokines comprise rheumatoid arthritis, rheumatoid spondylitis, spondyloarthropathies, systemic lupus erythematosus, osteoarthritis, gouty arthritis, juvenile arthritis and other arthritic conditions, polychondritis, sclerodoma, Wegener granulamatosis, dermatomyositis, Steven-Johnson syndrome, idiopatic sprue, endocrine opthalmopathy, Graves' disease, alveolitis, chronic hypersensitivity pneumonitis, primary billiary cirrhosis, uveitis, keratoconjunctivitis sicca and vernal keratoconjunctivitis, allergic rhinitis, pemphigus, eosinophilia, Loffler's syndrome, eosinophilic pneumonia, parasitic infestation, bronchopulmonary aspergillosis, polyarteritis nodosa, eosinophilic granuloma, eosinophil-related disorders affecting the airways occasioned by drug-reaction, sepsis, septic shock, endotoxic shock, gram negative sepsis, toxic shock syndrome, cerebral malaria, adult respiratory distress syndrome, bronchitis (acute, arachidic, catarrhal, chronic, croupus, phthinoid bronchitis), chronic obstructive airway or pulmonary disease, pulmonary fibrosis, tuberculosis, pneumoconiosis (aluminosis, anthracosis, asbestosis, chalicocis, ptilosis, siderosis, silicosis, tobaccosis, byssinosis), exacerbation of airways hyperreactivity to other drug therapy (e.g. aspirin or β-agonist therapy), silicosis, pulmonary sarcoidosis, bone resorption diseases, meningitis, allergic encephalitis, reperfusion injury, graft versus host reaction, allograft rejections, transplant rejections, musculoskeletal and connective tissue diseases, fever and myalgias due to infection, such as influenza, cachexia (consequential to, e.g. bacterial, viral or parasitic, infection or to deprivation or deterioration of humoral or other organic function, or secondary to malignancy; malarial and vermal cachexia; cachexia resulting from dysfunction of the pituitary, thyroid or thymus glands as well as uremic cachexia; cachexia secondary to acquired immune deficiency syndrome (AIDS)), AIDS, ARC (AIDS related complex), diabetes, cancer, angiogenesis, lymphoma, Kawasaki syndrome, Behçet's syndrome, aphthous ulceration, skin-related disorders such as psoriasis, eczema, burns, dermatitis, keloid formation, scar tissue formation, erythema nodosum leprosum, Crohn's disease, ulcerative colitis, inflammatory bowel disease, irritable bowel syndrome, pyresis, asthma (intrinsic, extrinsic, allergic, non-atopic, exercise induced and occupational and bacterial infection induced asthma), wheezy infant syndrome, multiple sclerosis, Parkinson's disease, pancreatitis, cardiac disease, congestive heart failure, myocardial infarction, acute liver failure, glomerulonephritis, therapy-associated syndromes comprising Jarisch-Herxheimer reaction, and syndromes associated with IL-2 infusion, anti-CD3 antibody infusion, hemodialysis, yellow fever vaccination, HIV or other viral infections, such as Hepatitis C, CMV, influenza and herpes virus infections, pseudorabies and rhinotracheitis, angiofollicular lympoid hyperplasia, anemia (haemolytic, aplastic, pure red cell, idiopatic thrombocytopenia), neutropenia, lymphopenia, hepatosplenomegaly with mononuclear cell infiltration and pulmonary edema with interstitial cell infiltrates; or to prevent these diseases. In particular, the compounds of formula (I) or (I') can be used to treat rheumatoid arthritis, Crohn's disease, irritable bowel disease, colitis, psoriasis or multiple sclerosis.

The cytokine production inhibitory activity of the compounds of formula (I) or (I') such as the inhibition of TNF-α and/or IL-12 production, may be demonstrated in the in vitro test "Inhibition of cytokine production in human whole blood cultures". Suitable in vivo tests are "Determination of cytokine in serum of LPS (lipopolysaccharide) and anti-CD3 challenged mice", "Inhibition of LPS-galactosamine induced shock in mice", "Inhibition of collagen induced arthritis in mice".

The compounds of formula (I) or (I') may also inhibit Interleukin-6 (IL-6).

The present compounds may also act as intermediates for the preparation of further thiazolyl derivatives.

In view of the above described pharmacological properties, the compounds of formula (I) or (I') or any subgroup thereof, their N-oxides, pharmaceutically acceptable addition salts, quaternary amines and stereochemically isomeric forms, may be used as a medicine. In particular, the present compounds can be used for the manufacture of a medicament for treating or preventing diseases mediated through cytokines, more in particular diseases mediated through TNF-α and/or IL-12, such as inflammatory and auto-immune diseases.

In view of the utility of the compounds of formula (I) or (I'), there is provided a method of treating warm-blooded animals, including humans, suffering from or a method of preventing warm-blooded animals, including humans, to suffer from diseases mediated through cytokines, in particular mediated through TNF-α and/or IL-12, such as inflammatory and auto-immune diseases. Said methods comprise the administration, preferably oral administration, of an effective amount of a compound of formula (I) or (I'), a N-oxide form, a pharmaceutically acceptable addition salt, a quaternary amine or a possible stereoisomeric form thereof, to warm-blooded animals, including humans.

The present invention also provides compositions for preventing or treating diseases mediated through cytokines, in particular TNF-α and/or IL-12 comprising a therapeutically effective amount of a compound of formula (I) and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

To aid solubility of the compounds of formula (I), suitable ingredients, e.g. cyclodextrins, may be included in the compositions. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of formula (I) and one or more appropriate pharmaceutically acceptable water-soluble polymers.

The term "a solid dispersion" used hereinafter defines a system in a solid state (as opposed to a liquid or gaseous state) comprising at least two components, in casu the compound of formula (I) and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermodynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of formula (I), or amorphous, microcrystalline or crystalline water-soluble polymer, or both, are dispersed more or less evenly in another phase comprising water-soluble polymer, or compound of formula (I), or a solid solution comprising compound of formula (I) and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation.

The solution-evaporation process comprises the following steps a) dissolving the compound of formula (I) and the water-soluble polymer in an appropriate solvent, optionally at elevated temperatures;

b) heating the solution resulting under point a), optionally under vacuum, until the solvent is evaporated. The solution may also be poured onto a large surface so as to form a thin film, and evaporating the solvent therefrom.

In the spray-drying technique, the two components are also dissolved in an appropriate solvent and the resulting solution is then sprayed through the nozzle of a spray dryer followed by evaporating the solvent from the resulting droplets at elevated temperatures.

The preferred technique for preparing solid dispersions is the melt-extrusion process comprising the following steps:

a) mixing a compound of formula (I) and an appropriate water-soluble polymer, b) optionally blending additives with the thus obtained mixture, c) heating and compounding the thus obtained blend until one obtains a homogenous melt, d) forcing the thus obtained melt through one or more nozzles; and e) cooling the melt till it solidifies.

The terms "melt" and "melting" should be interpreted broadly. These terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products can be optionally milled and sieved.

The solid dispersion product may be milled or ground to particles having a particle size of less than 600 µm, preferably less than 400 µm and most preferably less than 125 µm.

The particles prepared as described hereinabove can then be formulated by conventional techniques into pharmaceutical dosage forms such as tablets and capsules.

It will be appreciated that a person of skill in the art will be able to optimize the parameters of the solid dispersion preparation techniques described above, such as the most appropriate solvent, the working temperature, the kind of apparatus being used, the rate of spray-drying, the throughput rate in the melt-extruder The water-soluble polymers in the particles are polymers that have an apparent viscosity, when dissolved at 20° C. in an aqueous solution at 2% (w/v), of 1 to 5000 mPa·s more preferably of 1 to 700 mPa·s, and most preferred of 1 to 100 mPa·s. For example, suitable water-soluble polymers include alkylcelluloses, hydroxyalkyl-celluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gummi arabicum, guar gummi and xanthan gummi, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, combinations of polyvinylalcohol and polyvinylpyrrolidone, polyalkylene oxides and copolymers of ethylene oxide and propylene oxide. Preferred water-soluble polymers are hydroxypropyl methylcelluloses.

Also one or more cyclodextrins can be used as water soluble polymer in the preparation of the above-mentioned particles as is disclosed in WO 97/18839. Said cyclodextrins include the pharmaceutically acceptable unsubstituted and substituted cyclodextrins known in the art, more particularly α, β or γ cyclodextrins or the pharmaceutically acceptable derivatives thereof.

Substituted cyclodextrins which can be used to prepare the above described particles include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxymethyl or carboxyethyl.

Of particular utility are the β-cyclodextrin ethers, e.g. dimethyl-β-cyclodextrin as described in Drugs of the Future, Vol. 9, No. 8, p. 577-578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

Another type of substituted cyclodextrins is sulfobutylcyclodextrines.

The ratio of the compound of formula (I) over the water soluble polymer may vary widely. For example ratios of 1/100 to 100/1 may be applied. Interesting ratios of the compound of formula (I) over cyclodextrin range from about 1/10 to 10/1. More interesting ratios range from about 1/5 to 5/1.

It may further be convenient to formulate the compounds of formula (I) in the form of nanoparticles which have a surface modifier adsorbed on the surface thereof in an amount sufficient to maintain an effective average particle size of less than 1000 nm.

Useful surface modifiers are believed to include those which physically adhere to the surface of the compound of formula (I) but do not chemically bond to said compound.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds of formula (I) involves a pharmaceutical composition whereby the compounds of formula (I) are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and a compound of formula (I) and optionally a seal-coating layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The present compounds are orally active compounds, and are preferably orally administered.

The exact dosage and frequency of administration depends on the particular compound of formula (I) or (I') used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds of formula (I) or (I') may also be used in combination with other conventional anti-inflammatory or immunosuppressive agents, such as steroids, cyclooxygenase-2 inhibitors, non-steroidal-anti-inflammatory drugs, TNF-α antibodies, such as for example acetyl salicylic acid, bufexamac, diclofenac potassium, sulindac, diclofenac sodium, ketorolac trometamol, tolmetine, ibuprofen, naproxen, naproxen sodium, tiaprofen acid, flurbiprofen, mefenamic acid, nifluminic acid, meclofenamate, indomethacin, proglumetacine, ketoprofen, nabumetone, paracetamol, piroxicam, tenoxicam, nimesulide, fenylbutazon, tramadol, beclomethasone dipropionate, betamethasone, beclamethasone, budesonide, fluticasone, mometasone, dexamethasone, hydrocortisone, methylprednisolone, prednisolone, prednisone, triamcinolone, celecoxib, rofecoxib, infliximab, leflunomide, etanercept, CPH 82, methotrexate, sulfasalazine, antilymphocytory immunoglobulines, antithymocytory immunoglobulines, azathioprine, cyclosporine, tacrolimus substances, ascomycin, rapamycin, muromonab-CD3.

Thus, the present invention also relates to the combination of a compound of formula (I) or (I') and another anti-inflammatory or immunosuppressive agent. Said combination may be used as a medicine. The present invention also relates to a product containing (a) a compound of formula (I) or (I'), and (b) another anti-inflammatory or immunosuppressive compound, as a combined preparation for simultaneous, separate or sequential use in the treatment of diseases related to an excessive or unregulated cytokine production. The different drugs may be combined in a single preparation together with pharmaceutically acceptable carriers.

EXPERIMENTAL PART

Hereinafter, "DMF" is defined as N,N-dimethylformamide, "DIPE" is defined as diisopropyl ether, "THF" is defined as tetrahydrofuran.

A. Preparation of the Intermediate Compounds

Example A1 a) Preparation of Intermediate 1

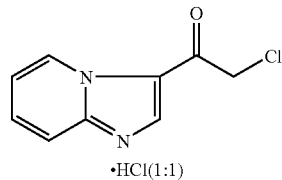

·HCl(1:1)

AlC₃ (50 g) was added portionwise to a solution of imidazo[1,2-a]pyridine (0.05 mol) in CS₂ (250 ml). The mixture was warmed to ±40° C. Then, chloroacetyl chloride (0.11 mol) in CS₂ (50 ml) was added dropwise and the resulting reaction mixture was stirred and refluxed overnight. The reaction mixture was cooled, then cooled on an ice/ethanol-bath and decomposed by dropwise addition of ice-water. CH₃OH (100 ml) was added dropwise and the reaction mixture was stirred for 3 hours at room temperature. The resulting precipitate was filtered off and dried (vacuum). Yield: 7.3 g of intermediate 1 (63%).

b) Preparation of Intermediate 2

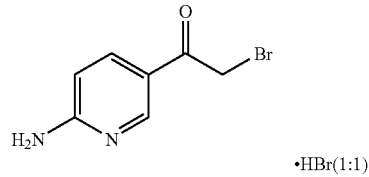

·HBr(1:1)

1-(6-amino-3-pyridinyl)ethanone hydrobromide (0.007 mol) was dissolved in THF, p.a. (50 ml)/CH₃OH, p.a. (10 ml) and the mixture was stirred at room temperature. N,N,N-trimethylbenzenaminium tribromide (0.007 mol) was added portionwise and the reaction mixture was stirred overnight at room temperature. The solvent was evaporated. The residue was stirred in 2-propanone/2-propanol, filtered off and dried. Yield: 1.85 g of intermediate 2 (88.6%).

Example A2 a) Preparation of Intermediate 3

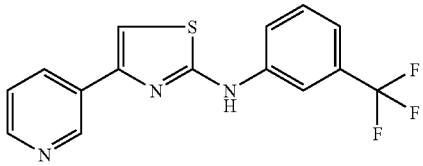

A mixture of 2-bromo-1-(3-pyridinyl)ethanone hydrobromide (0.0030 mol) and [3-(trifluoromethyl)phenyl]thiourea (0.0030 mol) in ethanol (30 ml) was stirred and refluxed for 4 hours, then allowed to cool while stirring. The mixture was filtered and the filter residue washed with ethanol, then 2-propanone. The residue was taken up into CH₃OH/CH₂Cl₂/(H₂O/Na₂CO₃/NaOAc) and stirred for 10 minutes until most material had dissolved. The layers were separated. The aqueous phase was extracted with CH₂Cl₂ (the remaining solid material then dissolved) (×4). The combined organic layers were dried (MgSO₄), filtered and the solvent was evaporated. Yield: 0.84 g of intermediate 3 (88%; mp: 204-206° C.).

b) Preparation of Intermediate 4

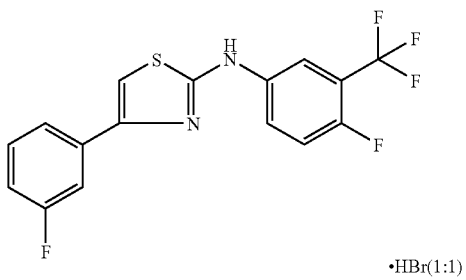

1-(3-fluorophenyl)ethanone (0.0082 mol) in THF (50 ml) was stirred at room temperature. N,N,N-trimethylbenzenaminium tribromide (0.0082 mol) was added portionwise over 1 hour. The formed precipitate was filtered off and washed. The filtrate was stirred at room temperature. [4-fluoro-3-(trifluoromethyl)phenyl]thiourea (0.0082 mol) was added. The mixture was stirred for 18 hours. The solvent was evaporated. The residue was crystallized from CH₃CN (25 ml). The precipitate was filtered off, washed with DIPE and dried. Yield: 1.7 g. This fraction was recrystallized from CH₃CN (25 ml). The precipitate was filtered off, washed with DIPE and dried. Yield: 1.3 g of intermediate 4.

c) Preparation of Intermediate 5

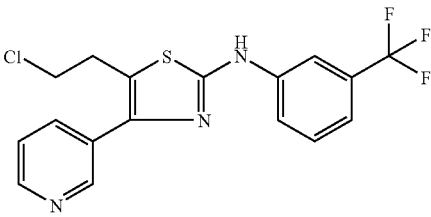

A solution of intermediate 14 (0.005 mol) (prepared according to Example A8b), [3-(trifluoromethyl)phenyl]thiourea (0.005 mol) in methanol (50 ml) was stirred and refluxed for 14 hours. The reaction mixture was cooled. The precipitate was filtered off and dried. Yield: 1.5 g of intermediate 5.

Example A3 a) Preparation of Intermediate 6

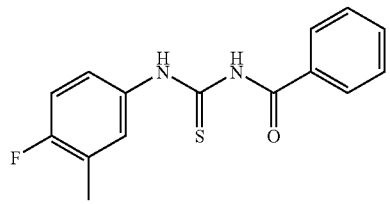

A solution of benzoyl isothiocyanate (0.068 mol) in THF (50 ml) was added dropwise to a solution of 4-fluoro-3-methyl-benzenamine (0.068 mol) in THF (150 ml). The reaction mixture was stirred overnight at room temperature. The solvent was evaporated. The residue was suspended in DIPE, filtered off, washed and dried (vacuum). Yield: intermediate 6.

b) Preparation of intermediate 7

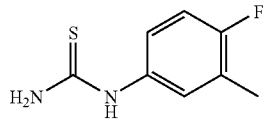

A mixture of intermediate 6 (0.055 mol) and NaOH 1M (0.06 mol) in EtOH (500 ml) was stirred and refluxed for 1 hour. The reaction mixture was cooled and the solvent was evaporated. The residue was suspended in H₂O, filtered off, washed and dried (vacuum). Yield: 9.8 g of intermediate 7 (97%).

Example A4

Preparation of Intermediate 8

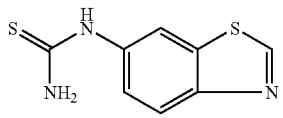

A mixture of benzoyl isothiocyanate (0.027 mol) in THF p.a. (10 ml) was added dropwise at room temperature to a mixture of 6-benzothiazolamine (0.027 mol) in THF p.a. (80 ml). The mixture was stirred at room temperature for 2 hours. The solvent was evaporated. EtOH (100 ml) was added to the residue. The mixture was warmed up. NaOH 1M p.a. (0.027 mol) was added dropwise. The mixture was stirred while the temperature was brought to room temperature. The precipitate was filtered off and dried. Yield: 4 g. The filtrate was evaporated. Yield: 5 g F1. The filtered precipitate and F1 were combined and stirred in water. The precipitate was filtered off and dried. Yield: 5 g of intermediate 8 (88%).

Example A5 a) Preparation of Intermediate 9

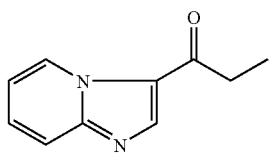

·HBr (1:1)

A mixture of imidazo[1,2-a]pyridine (0.42 mol) in $CH_2Cl_2$ (1000 ml) was cooled to 5° C. (ice/EtOH). $AlCl_3$ (150 g) was added portionwise (temp. rise to 30° C.). A mixture of propanoyl chloride (0.84 mol) in $CH_2Cl_2$ (500 ml) was added dropwise at 10° C. over 30 minutes. The mixture was stirred and refluxed for 48 hours and then cooled. Ice/MeOH (1000 ml) was added dropwise. The mixture was stirred for 4 hours. The organic layer was separated and the solvent was evaporated. The residue was stirred in 2-propanone, filtered and dried in vacuo at 40° C. Yield: 64.79 g of intermediate 9 (73%).

b) Preparation of Intermediate 10

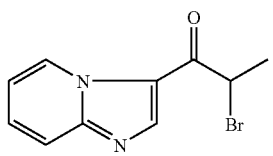

·HBr (1:1)

HBr 48% in $H_2O$ (50 ml) was added to a mixture of intermediate 9 (0.095 mol) in HOAc (150 ml). The mixture was warmed up to 70° C. $Br_2$ (0.095 mol) was added dropwise. The mixture was stirred for 14 hours at 70° C. and then cooled. The solvent was evaporated. The residue was co-evaporated with EtOH/toluene. The residue was stirred in 2-propanone. The precipitate was filtered off and dried at 40° C. in vacuo. The residue (12.682 g) was stirred in refluxing 2-propanone. EtOH was added until the reaction mixture was homogeneous. The mixture was allowed to cool. The precipitate was filtered off and dried in vacuo at 50° C. Yield: 100% of intermediate 10.

Example A6

Preparation of Intermediate 11

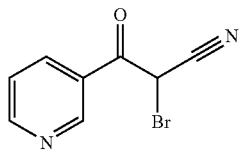

Reaction under $N_2$ atmosphere. A mixture of sodium β-oxo-3-pyridinepropanenitrile ion (1⁻) (0.005 mol) in $CH_2Cl_2$, p.a. was stirred at −70° C. $Br_2$ (0.005 mol) in $CH_2Cl_2$, p.a. (10 ml) was added dropwise over 30 minutes at −70° C. The mixture was allowed to warm to room temperature. The mixture was stirred overnight at 20° C. $CH_2Cl_2$ (100 ml) was added. The mixture was filtered and the filtrate was evaporated (at low temperature). Yield: 1 g (91%) of intermediate 11.

Example A7

Preparation of Intermediate 12

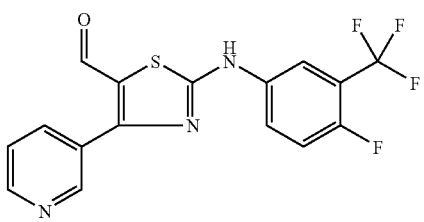

A mixture of compound 99 (0.0141 mol) in tetrahydrofuran (125 ml) was stirred under $N_2$ on an isopropanol/$CO_2$ cooling bath. Tetrahydrofuran (100 ml) was added and stirring was continued till a temperature of −78° C. nBuLi was added dropwise. After addition, the reaction mixture was stirred further at −78° C. for at least 1 hour, then DMF (11 ml) was added dropwise. After addition, stirring was continued at −78° C. for another hour. Then, the reaction mixture was allowed to reach −15° C. and 100 ml of HCl 1N+100 ml of ice water was added dropwise. After addition, stirring was continued for 30 minutes followed by extraction with 500 ml of ethyl acetate. $K_2CO_3$ was added to the separated aqueous layer till a pH of approximately 9 was reached and the mixture was again extracted with 100 ml of ethyl acetate. The combined organic layers were dried ($MgSO_4$), filtered and evaporated. The residue was stirred in 50 ml of boiling acetonitrile/

CH$_2$Cl$_2$ 3/1. The residue was filtered off, washed with acetonitrile and dried at 50° C. (vacuum). Yield: 3.08 g of intermediate 12.

Example A8 a) Preparation of Intermediate 13

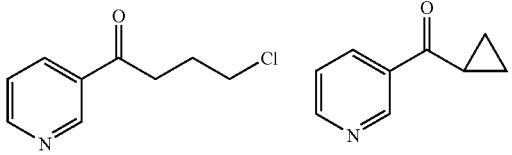

(0.14 mol) and HCl 12 N (240 ml) were stirred and refluxed. The solvent was evaporated and the residue was taken up in ice/CH$_2$Cl$_2$. The mixture was alkalized with Na$_2$CO$_3$. The organic layer was separated, washed with H$_2$O, dried, filtered and evaporated. The residue was purified on SiO$_2$ (eluent: CH$_2$Cl$_2$/CH$_3$OH). The desired fraction was evaporated. Yield: 15 g of intermediate 13.

b) Preparation of Intermediate 14

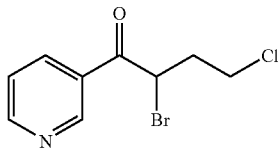

Br$_2$ (0.08 mol) was added dropwise to a mixture of intermediate 13 (15 g) and acetic acid (60 ml) and stirring was continued overnight at room temperature. The solvent was evaporated and the residue was crystallized from diisopropyl ether. The precipitate was filtered off and dried. Yield: 14 g of intermediate 14.

Example A9

Preparation of

Intermediate 15

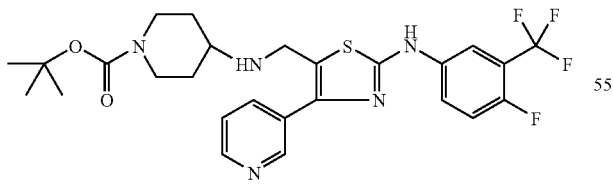

A solution of compound 93 (0.00122 mol) and 1-tert.butoxycarbonyl-4-piperidinone (0.3 g) in thiophene solution (0.1 ml) and methanol (50 ml) was hydrogenated with H2 (1 eq.) over Pd/C 10% (0.1 g). The catalyst was filtered off. The filtrate was evaporated and co-evaporated with toluene. The residue was purified over silica using CH$_2$Cl$_2$/MeOH 96/4 as eluent. The desired fractions were combined and evaporated. The solid was crystallized from 10 ml of diisopropyl ether, filtered off, washed and dried at 50° C. (vacuum). Yield: 0.276 g of intermediate 15.

B. Preparation of the Final Compounds

Example B1 a) Preparation of Compound 11

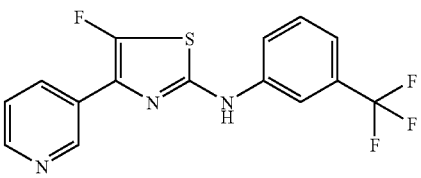

Intermediate 3 (0.016 mol) was dissolved in DMF (40 ml), cooled to 5° C. and then 1-(chloromethyl)-4-fluoro-1,4-diazoniabicyclo[2.2.2]octane bis[tetrafluoroborate(1⁻)] (=Selectfluor®) (0.017 mol) was added in one portion. The reaction mixture was stirred and allowed to warm slowly to room temperature and stirred further for 24 hours. A NH$_3$/MeOH-solution and H$_2$O was added while rapid stirring and cooling and the mixture was stirred for 6 hours. The mixture was poured out into H$_2$O (100 ml), filtered and washed with H$_2$O. The residue was purified by flash column chromatography over silica gel (eluent: THF/hexane 20/80). The product fractions were collected and the solvent was evaporated. The residue was dried (24 hours, 20° C., vacuum). Yield: 2.19 g of compound 1 (40%; mp 208-210° C.).

b) Preparation of Compound 2

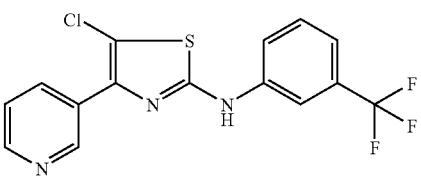

•HCl (1:1)

Intermediate 3 (0.0026 mol) was dissolved in DMF (10 ml), then cooled to ±0° C. 1-Chloro-2,5-pyrrolidinedione (0.0026 mol) was added in one shot. The reaction mixture was stirred for 2 hours, allowing to warm to room temperature. The solvent was evaporated. The residue was triturated under water+Na$_2$CO$_3$ (aq.), filtered off, washed with water, CH$_3$CN, then dissolved in ethanol (150 ml). The solution was filtered and the filtrate was acidified (to pH=1) with HCl/2-propanol. The solvent was evaporated. Yield: 0.30 g of compound 2 (29%).

In order to prepare 5-bromo derivatives, such as compound 99, 1-bromo-2,5-pyrrolidinedione can be used.

c) Preparation of Compound 3

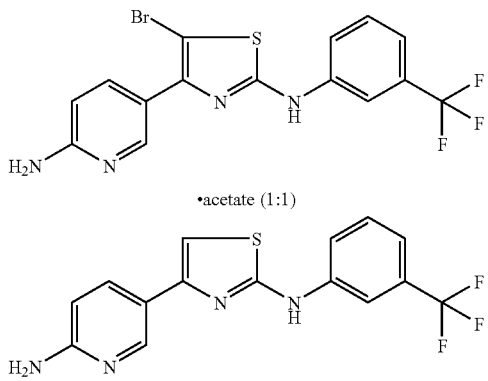

•acetate (1:1)

(0.03 mol, crude residue, containing Br⁻)(prepared according to A2a) in DMF (50 ml) was stirred until dissolution. Selectfluor® (0.003 mol) was added portionwise and the mixture was stirred overnight at room temperature. The solvent was evaporated and coevaporated with toluene. The residue was stirred in toluene. The precipitate was filtered off and dried. Yield: 1.2 g. The filtrate was purified by column chromatography over silica gel (eluent: $CH_2Cl_2$/MeOH 98/2; 90/10). The desired fractions were collected and the solvent was evaporated. The residue was recrystallized from $CH_3CN$. The precipitate was filtered off and dried. Yield: 0.34 g. This fraction was dried overnight (80-90° C.; vacuum). Yield: 0.3 g of compound 3.

Example B2 a) Preparation of Compound 5

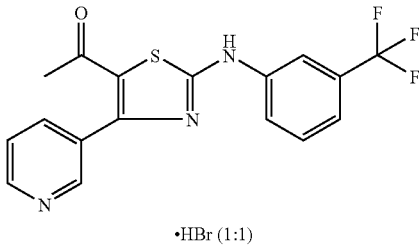

•HBr (1:1)

1-(3-Pyridinyl)-1,3-butanedione (0.01 mol) in THF (200 ml) was stirred. N,N,N-trimethylbenzenaminium tribromide (0.01 mol) was added portionwise at 20° C. The mixture was stirred for 45 minutes. EtOH (100 ml) was added and the mixture was stirred for 15 minutes. [3-(Trifluoromethyl)phenyl]thiourea (0.01 mol) was added. The mixture was stirred overnight at 20° C.; then stirred and refluxed. The mixture was stirred for 1 hour. The precipitate was filtered off and dried. Yield: 0.6 g. The filtrate's solvent was evaporated. The residue was crystallized from 2-propanol. The precipitate was filtered off and dried. Yield: 1.5 g of compound 5 (34%).

b) Preparation of Compound 6

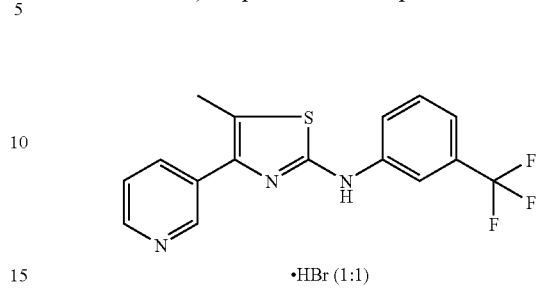

•HBr (1:1)

A mixture of 2-bromo-1-(3-pyridinyl)-1-propanone hydrobromide (0.005 mol) and [3-(trifluoro)phenyl]thiourea (0.005 mol) in EtOH (50 ml) was stirred and refluxed for 8 hours. The reaction mixture was cooled, filtered, washed with EtOH and 2-propanone and then dried (60° C., vacuum, 16 hours). Yield: 1.52 g of compound 6 (73%).

c) Preparation of compound 7

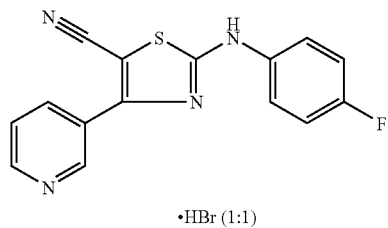

•HBr (1:1)

A mixture of intermediate 11 (0.007 mol) and (4-fluorophenyl)thiourea (0.008 mol) in ethanol (150 ml) was stirred and refluxed for 4 hours, then stirred overnight at 20° C. The precipitate was filtered off, washed with 2-propanol, and dried. Yield: 0.8 g of compound 7 (30%).

d-1) Preparation of Compound 8

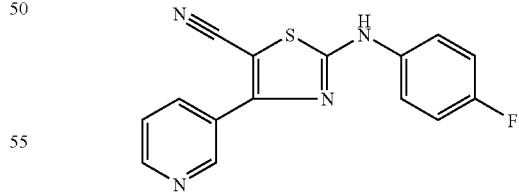

A mixture of sodium β-oxo-3-pyridinepropanenitrile ion (1⁻) (0.029 mol) in $CH_2Cl_2$, p.a. (100 ml) was stirred at −60° C. A solution of $Br_2$ (0.029 mol) in $CH_2Cl_2$, p.a. (20 ml) was added dropwise at −60° C. and the reaction mixture was allowed to warm to room temperature. A solution of (4-fluorophenyl)thiourea (0.029 mol) in $CH_2Cl_2$, p.a. (50 ml) was added. Ethanol (100 ml) was added and the reaction mixture was stirred overnight. The solvent was evaporated. The resid-2) Preparation of Compound 96

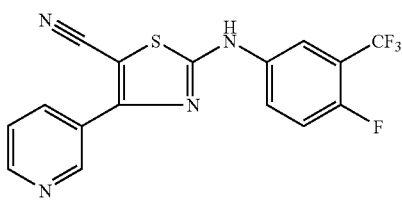

To a stirring mixture of sodium β-oxo-3-pyridinepropanenitrile ion (1⁻) (0.088 mol) and tetrahydrofuran (250 ml) under N₂ atmosphere, phenyl trimethyl ammonium tribromide ((0.088 mol) was added portionwise. After addition, the reaction mixture was stirred further for 3 hours at room temperature. (4-fluoro-3-trifluoromethyl-phenyl)thiourea (0.084 mol) was added followed by the addition of ethanol (100 ml). The reaction mixture was stirred further at room temperature for 3 hours, refluxed for 3 hours and stirred further at room temperature for 16 hours. Tetrahydrofuran (150 ml) was added and stirring continued for 1 hour. The mixture was filtered and the residue washed with tetrahydrofuran. The residue was then stirred in boiling acetonitrile (75 ml)/H₂O (100 ml)/NaHCO₃ aqueous saturated solution (50 ml) for 30 minutes. The mixture was filtered at 35° C., the residue washed with acetonitrile-H₂O (½), with H₂O, with ethanol and with diisopropyl ether. The residue was dried at 60° C. (vacuum). Yield: 11.74 g of compound 96.

Example B3

Preparation of Compound 9

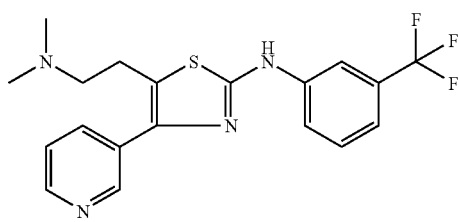

A mixture of

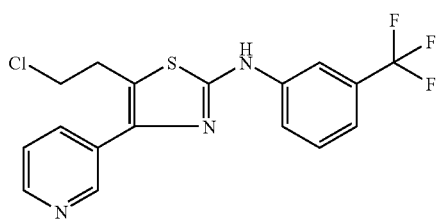

(interm. 5; prepared according to A2.c) (0.0025 mol), N-methylmethanamine hydrochloride (0.003 mol) and NaHCO₃ (0.01 mol) in CH₃CN (25 ml) was stirred overnight at 50° C. More N-methylmethanamine hydrochloride (0.012 mol) and NaHCO₃ (0.0125 mol) were added and the mixture was stirred at 70° C. for 48 hours (in pressure tube). The mixture was cooled. The solvent was evaporated. The residue was dissolved in CH₂Cl₂ and washed with H₂O. The separated organic layer was dried, filtered and the solvent was evaporated. The residue was purified by column chromatography over silica gel (eluent: CH₂Cl₂/MeOH 98/2). The desired fractions were collected and the solvent was evaporated. The residue was triturated under DIPE. The precipitate was filtered off and dried. Yield: 0.1 g of compound 9.

Example B4

Preparation of Compound 10

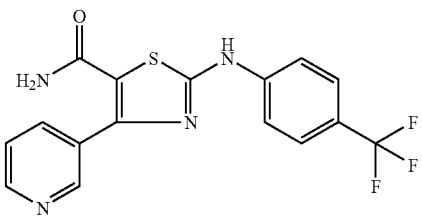

H₂SO₄/H₂O 90/10 (50 ml) was stirred in a reaction flask. Then, compound 84 (prepared according to B2.c) (0.0082 mol) was added portionwise at 20° C. The reaction mixture was heated to ±70° C., then stirred overnight at 20° C. The mixture was re-heated and stirred for one hour at 70° C., then for 3 hours at 20° C. The mixture was poured out onto ice and this mixture was alkalized with a NH₄OH (conc.) and left overnight. The precipitate was filtered off, washed with H₂O and dried. The residue was crystallized from DMF/methanol, filtered off and dried. Yield: 1.5 g of compound 10.

Example B5

Preparation of Compound 11

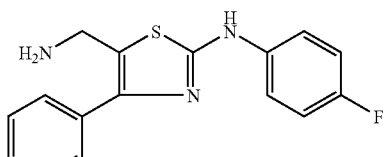

A mixture of compound 8 (prepared according to B2.d) (0.014 mol) in NH₃/CH₃OH (150 ml) and THF (50 ml) was hydrogenated at 14° C. with Raney Nickel (catalytic quantity). After uptake of H₂ (2 equiv), the catalyst was filtered off and the filtrate was evaporated. The residue was stirred in 2-propanol, filtered off and dried. Yield: 2.8 g. Part (0.5 g) of this fraction was purified by column chromatography over silica gel (eluent: CH₂Cl₂/CH₃OH 97/3). The product fractions were collected and the solvent was evaporated. The residue was dried. Yield: 0.4 g of compound 11.

Example B6

Preparation of Compound 13

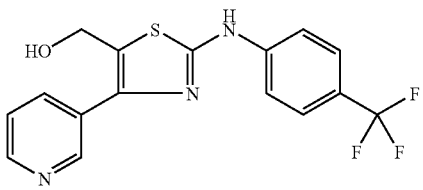

LiAlH$_4$ (0.007 mol) was suspended in THF (100 ml) and stirred at room temperature. Compound 12 (prepared according to B2.a) (0.0034 mol) was added and the mixture was stirred for 2 hours at room temperature. H$_2$O (5 ml) was added dropwise. NaOH (1N; 10 ml) was added dropwise. H$_2$O (50 ml) was added dropwise. The mixture was filtered over dicalite. The solvent was evaporated. The residue was taken up in CH$_2$Cl$_2$ and H$_2$O. The separated organic layer washed with H$_2$O, dried and filtered. The solvent was evaporated. The residue was purified by column chromatography over silica gel (eluent: CH$_2$Cl$_2$/MeOH 99/1). The desired fractions were collected and the solvent was evaporated. The residue was triturated. The precipitate was filtered off and dried. Yield: 0.1 g of compound 13.

Example B7

Preparation of Compound 14

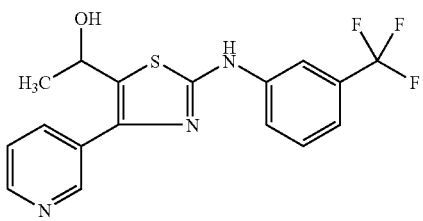

NaBH$_4$ (0.015 mol) was slowly added in 30 minutes at 20° C. to a mixture of compound 5 (prepared according to B2.a) (0.0034 mol) in methanol (100 ml). The mixture was stirred overnight. More NaBH$_4$ (0.5 g) was added dropwise at 20° C. Again the mixture was stirred overnight at 20° C. The reaction mixture was filtered, washed with water and then dried. Yield: 1.6 g of compound 15.

Example B8 a) Preparation of Compound 89

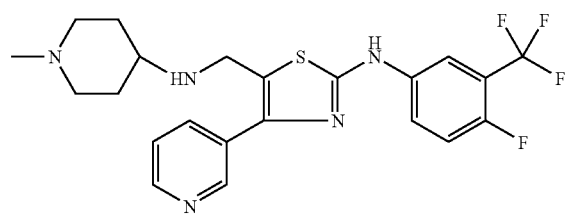

A mixture of compound 93 (0.2 g; 0.0005 mol), 1-methyl-4-piperidinone (0.1 g), Pd/C 10% (0.1 g), thiophene solution (0.1 ml) and methanol (50 ml) was stirred for 7 days at room temperature under H$_2$ (0.0005 mol). 1-methyl-4-piperidinone was added several times. The catalyst was filtered off, the residue was filtered over silica gel (eluent: CH$_2$Cl$_2$/CH$_3$OH/CH$_3$OH—NH$_3$ 95/5/0 to 90/10/0 to 90/5/0). The desired fractions were collected, the solvent was evaporated. The residue was purified by column chromatography (eluent: CH$_2$Cl$_2$/CH$_3$OH—NH$_3$ 95/5). The desired fractions were collected, the solvent was evaporated and the residue was dried. Yield: 0.044 g of compound 89.

b) Preparation of Compound 90 and Compound 91

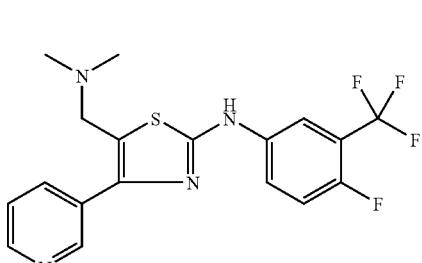

Compound 91

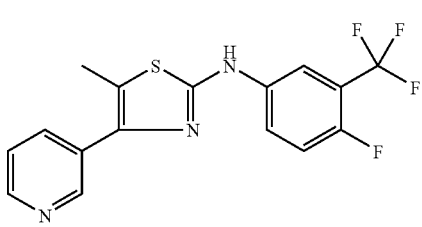

Compound 90

A mixture of compound 93 (0.5 g; 0.00135 mol), paraform (0.85 g), Pd/C 10% (0.9 g), thiophene solution (1 ml) and methanol (50 ml) was stirred at room temperature under H$_2$ (0.0027 mol). After 24 hours the catalyst was filtered off and the filtrate was evaporated. The residue was purified by column chromatography (eluent: CH$_2$Cl$_2$/CH$_3$OH—NH$_3$: 98/2 to 95/5). Two fractions (F1, F2) were collected. The solvent of F1 was evaporated, the residue was stirred in diisopropyl ether, filtered off and dried. Yield: 0.069 g of compound 90. The solvent of F2 was evaporated, the residue was stirred in CH$_2$Cl$_2$, filtered off and dried. Yield: 0.023 g of compound 91.

Example B9

Preparation of Compound 100 and Compound 101

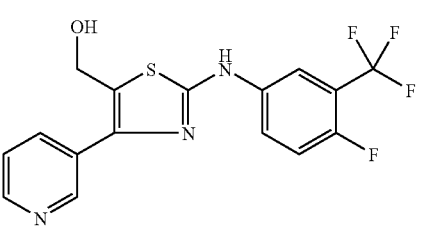

Compound 101

-continued

Compound 100

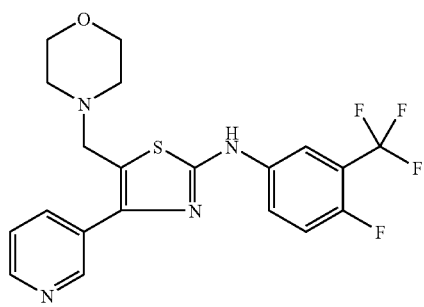

A mixture of intermediate 12 (0.0008 mol) and morpholine (0.006 mol) in methanol (50 ml) was hydrogenated at room temperature for 4 days with $Pt/C_5\%$ as a catalyst. After uptake of $H_2$ (1 equiv.), the catalyst was filtered off and the solvent was evaporated. The residue was purified by column chromatography over silica gel (eluent: $CH_2Cl_2$/MeOH 95/5) yielding two fractions. The two fractions were collected and the solvent was evaporated yielding residue I and II. Residue I was stirred in diisopropyl ether. The precipitate was filtered off and dried. Yield 0.079 g of compound 100. Residue II was dried. Yield: 0.056 g of compound 101.

Example B10

Preparation of Compound 88

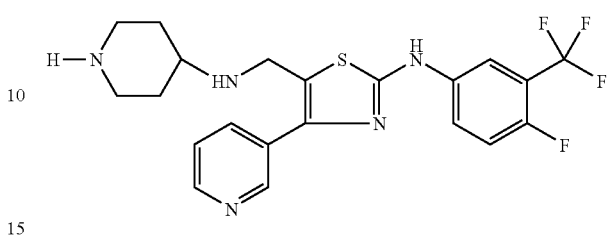

To a stirring solution of intermediate 15 (0.0005 mol) in isopropanol (10 ml) was added HCl 6 N in isopropanol (2 ml). The reaction mixture was stirred at 100° C. for 3½ hours and was then allowed to cool to room temperature. The solvent was evaporated. The residue was stirred in 10 ml of $NaHCO_3$ aqueous saturated solution+5 ml of $H_2O$ for 1 hour. The precipitate was filtered off, washed with $H_2O$ and dried at 50° C. Yield: 0.170 g of compound 88.

Table 1 lists compounds of formula (I) as prepared according to one of the above examples (Ex. No.).

TABLE 1

| Comp. No. | Ex. No. | L | Z | Q | Phys. properties |
|---|---|---|---|---|---|
| 3 | B1c | ![2-amino-5-methylpyridyl] | Br | ![3-CF3-phenyl] | •acetate(1:1) |
| 15 | B1c | ![3-fluoro-phenyl] | Br | ![2-CF3-4-F-phenyl] | |
| 5 | B2a | 3-pyridyl | —C(=O)CH₃ | ![3-CF3-phenyl] | •HBr(1:1) |
| 16 | B4 | 3-pyridyl | —C(=O)NH₂ | ![3-CF3-phenyl] | |
| 10 | B4 | 3-pyridyl | —C(=O)NH₂ | ![4-CF3-phenyl] | |
| 17 | B3 | 3pyridyl | ![morpholinopropyl] | ![3-CF3-phenyl] | |
| 14 | B7 | 3-pyridyl | —CH(OH)CH₃ | ![3-CF3-phenyl] | |

TABLE 1-continued
| Comp. No. | Ex. No. | L | Z | Q | Phys. properties |
|---|---|---|---|---|---|
| 18 | B5 | 3-pyridyl | —CH$_2$NH$_2$ | 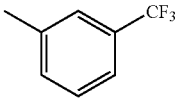 | •HCl(1:2) |
| 11 | B5 | 3-pyridyl | —CH$_2$NH$_2$ | 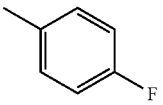 | |
| 19 | B6 | 4-pyridyl | —CH$_2$OH | 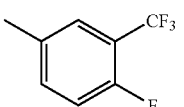 | |
| 13 | B6 | 3-pyridyl | —CH$_2$OH | 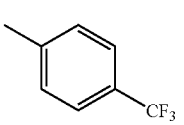 | |
| 2 | B1b | 3-pyridyl | Cl | 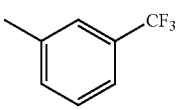 | •HCl(1:1) |
| 20 | B1b | 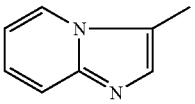 | Cl | 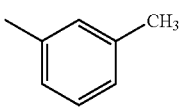 | |
| 21 | B1b | 3-pyridyl | Cl | 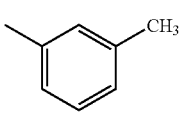 | |
| 22 | B1b | 3-pyridyl | Cl | 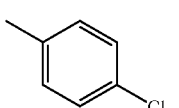 | |
| 23 | B1a | 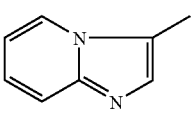 | F | 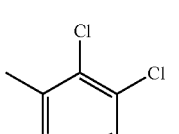 | •HCl(1:1)•H$_2$O (1:1) m.p.: 180° C. |
| 24 | B1a | 3-pyridyl | F | 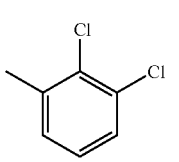 | m.p.: 226° C. |
| 25 | B1a | 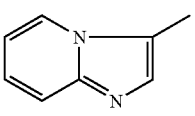 | F | 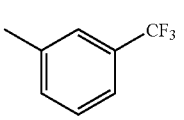 | |
| 4 | B1a | 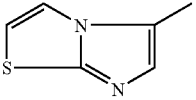 | F | 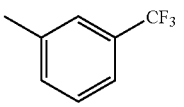 | m.p.: 210-215° C. |

TABLE 1-continued
| Comp. No. | Ex. No. | L | Z | Q | Phys. properties |
|---|---|---|---|---|---|
| 1 | B1a | 3-pyridyl | F | 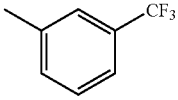 | |
| 26 | B1a | 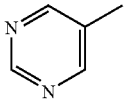 | F | 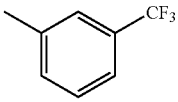 | |
| 27 | B1a | 3-pyridyl | F | 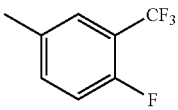 | |
| 28 | B1a | 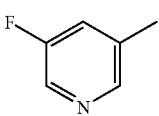 | F | 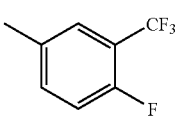 | |
| 29 | B1a | 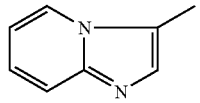 | F | 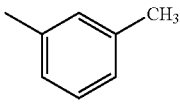 | •HCl(1:1) |
| 30 | B1a | 3-pyridyl | F | 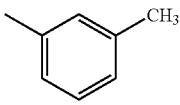 | |
| 31 | B1a | 3-pyridyl | F | 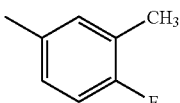 | m.p.: 176-178° C. |
| 32 | B1a | 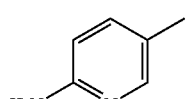 | F | 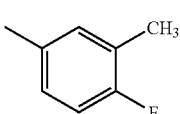 | •HCl(1:1) |
| 33 | B1a | 3-furyl | F | 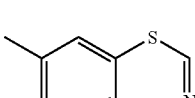 | |
| 34 | B1a | 3-pyridyl | F | 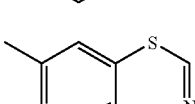 | •HBr(1:2) |
| 35 | B1a | 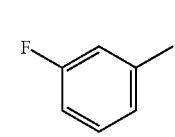 | F | 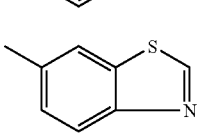 | |
| 36 | B1a | 3-pyridyl | F | 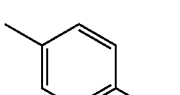 | |
| 37 | B2b | 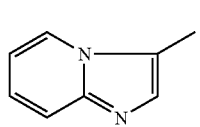 | CH$_3$ | 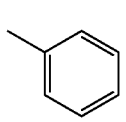 | •HBr(1:2) |

TABLE 1-continued
| Comp. No. | Ex. No. | L | Z | Q | Phys. properties |
|---|---|---|---|---|---|
| 38 | B2b | 3-pyridyl | CH$_3$ | 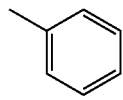 | •HBr(1:2) |
| 39 | B2b | 4-pyridyl | CH$_3$ | 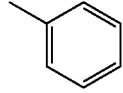 | •HBr(1:2) |
| 40 | B2b | 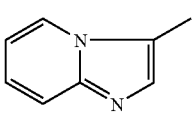 | CH$_3$ | 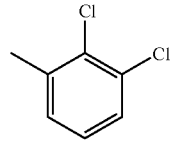 | •HBr(1:1) |
| 41 | B2b | 3-pyridyl | CH$_3$ | 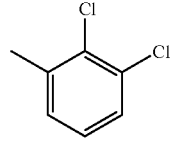 | •HBr(1:1) |
| 42 | B2b | 4-pyridyl | CH$_3$ | 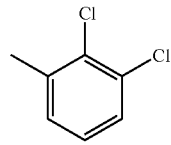 | •HBr(1:2) |
| 43 | B2b | 3-pyridyl | CH$_3$ | 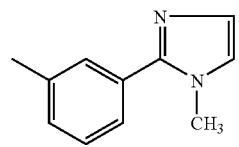 | •HBr(1:2) |
| 44 | B2b | 3-pyridyl | CH$_3$ | 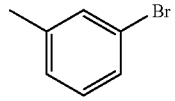 | •HBr(1:2) |
| 45 | B2b | 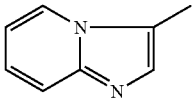 | CH$_3$ | 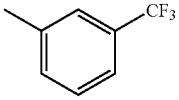 | •HBr(1:1) |
| 6 | B2b | 3-pyridyl | CH$_3$ | 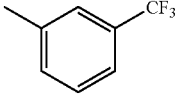 | •HBr(1:1) |
| 46 | B2b | 3-pyridyl | CH$_3$ | 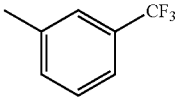 | •HBr(1:2) |
| 47 | B2b | 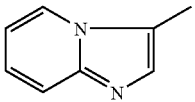 | CH$_3$ | 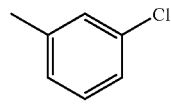 | •HBr(1:1) |

TABLE 1-continued
| Comp. No. | Ex. No. | L | Z | Q | Phys. properties |
|---|---|---|---|---|---|
| 48 | B2b | 3-pyridyl | CH₃ | 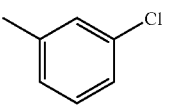 | •HBr(1:2) |
| 49 | B2b | 4-pyridyl | CH₃ | 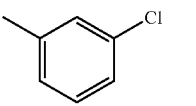 | •HBr(1:1) |
| 50 | B2b | 3-pyridyl | CH₃ | 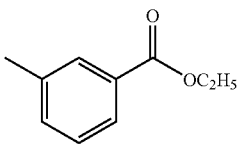 | |
| 51 | B2b | 3-pyridyl | CH₃ | 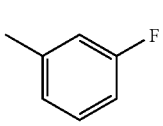 | |
| 52 | B2b | 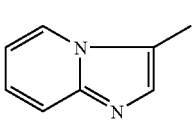 | CH₃ | 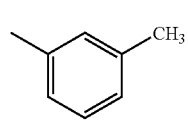 | |
| 53 | B2b | 3-pyridyl | CH₃ | 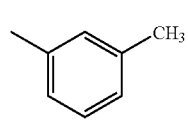 | |
| 54 | B2b | 3-pyridyl | CH₃ | 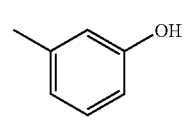 | |
| 55 | B2b | 3-pyridyl | CH₃ | 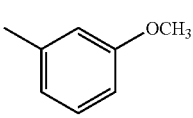 | |
| 56 | B2b | 3-pyridyl | CH₃ | 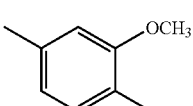 | |
| 57 | B2b | 3-pyridyl | CH₃ | 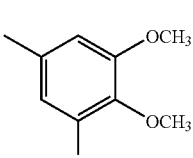 | |
| 58 | B2b | 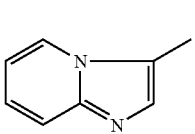 | CH₃ | 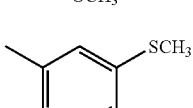 | |
| 59 | B2b | 3-pyridyl | CH₃ | 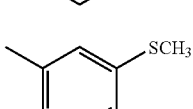 | |

TABLE 1-continued
| Comp. No. | Ex. No. | L | Z | Q | Phys. properties |
|---|---|---|---|---|---|
| 60 | B2b | 3-pyridyl | CH$_3$ | 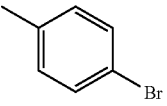 | |
| 61 | B2b | 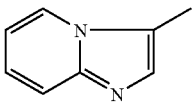 | CH$_3$ | 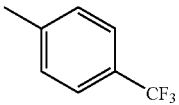 | |
| 62 | B2b | 3-pyridyl | CH$_3$ | 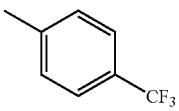 | •HBr(1:1) |
| 63 | B2b | 3-pyridyl | CH$_3$ | 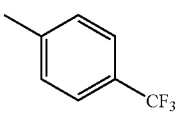 | |
| 64 | B2b | 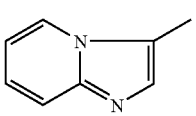 | CH$_3$ | 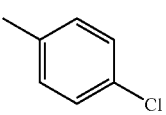 | •HBr(1:2) |
| 65 | B2b | 3-pyridyl | CH$_3$ | 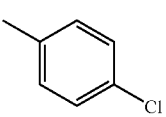 | •HBr(1:2) |
| 66 | B2b | 4-pyridyl | CH$_3$ | 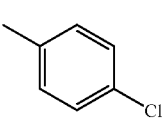 | •HBr(1:1) |
| 67 | B2b | 3-pyridyl | CH$_3$ | 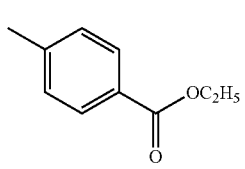 | |
| 68 | B2b | 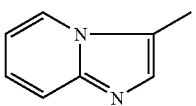 | CH$_3$ | 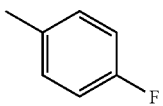 | |
| 69 | B2b | 3-pyridyl | CH$_3$ | 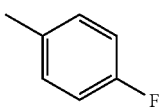 | |
| 70 | B2b | 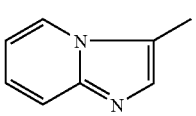 | CH$_3$ | 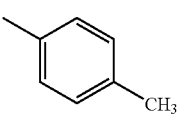 | |
| 71 | B2b | 3-pyridyl | CH$_3$ | 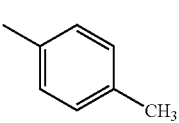 | |

TABLE 1-continued
| Comp. No. | Ex. No. | L | Z | Q | Phys. properties |
|---|---|---|---|---|---|
| 72 | B2b | 3-pyridyl | CH₃ | 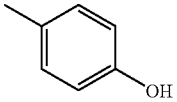 | |
| 73 | B2b | 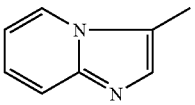 | CH₃ | 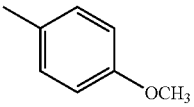 | |
| 74 | B2b | 3-pyridyl | CH₃ | 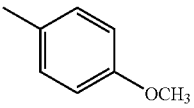 | |
| 75 | B2b | 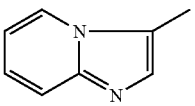 | CH₃ | 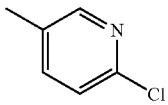 | |
| 76 | B2b | 3-pyridyl | CH₃ | 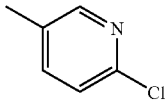 | |
| 77 | B2b | 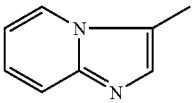 | CH₃ | 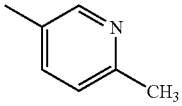 | |
| 78 | B2b | 3-pyridyl | CH₃ | 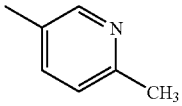 | |
| 79 | B2b | 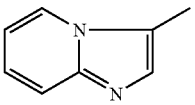 | CH₃ | 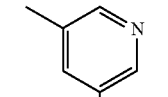 | |
| 80 | B2b | 3-pyridyl | CH₃ | 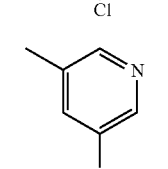 | |
| 81 | B2a | 4-pyridyl | CH₃—CH₂—O—C(=O)— | 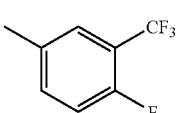 | |
| 9 | B3 | 3-pyridyl | (CH₃)₂N—CH₂—CH₂— | 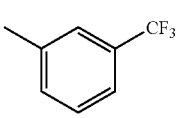 | |
| 82 | B2c | 3-pyridyl | CN | 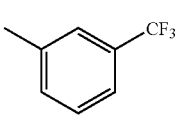 | HBr(1:1) |

TABLE 1-continued
| Comp. No. | Ex. No. | L | Z | Q | Phys. properties |
|---|---|---|---|---|---|
| 83 | B2c | 3-pyridyl | CN | 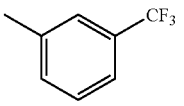 | HCl(1:1) |
| 84 | B2c | 3-pyridyl | CN | 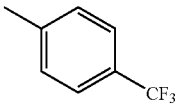 | HBr(1:1) |
| 7 | B2c | 3-pyridyl | CN | 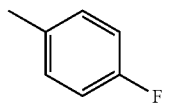 | HBr(1:1) |
| 8 | B2d-1 | 3-pyridyl | CN | 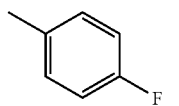 | |
| 85 | B2a | 3-pyridyl | CH$_3$—O—C(=O)— | 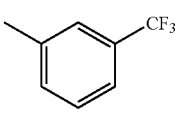 | m.p.: 252-254° C. |
| 12 | B2a | 3-pyridyl | CH$_3$—O—C(=O)— | 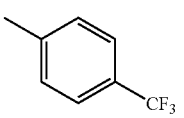 | HBr(1:1) |
| 86 | B2a | 3-pyridyl | CH$_3$—O—C(=O)— | 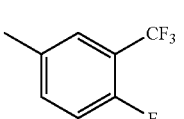 | |
| 87 | B9 | 3-pyridyl | CH$_3$CH$_2$—NH—CH$_2$— | 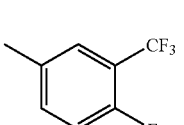 | |
| 88 | B10 | 3-pyridyl | 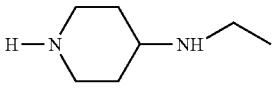 | 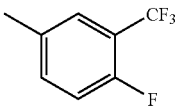 | |
| 89 | B8a | 3-pyridyl | 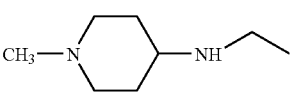 | 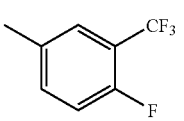 | |
| 90 | B8b | 3-pyridyl | CH$_3$ | 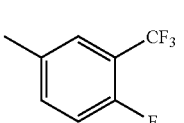 | |
| 91 | B8b | 3-pyridyl | (CH$_3$)$_2$N—CH$_2$— | 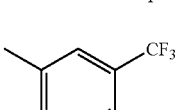 | |

TABLE 1-continued

| Comp. No. | Ex. No. | L | Z | Q | Phys. properties |
|---|---|---|---|---|---|
| 92 | B5 | 3-pyridyl | H₂N—CH₂— | 3-CF₃-4-methylphenyl | |
| 93 | B5 | 3-pyridyl | H₂N—CH₂— | 2-CF₃-4-methyl-1-F-phenyl | |
| 95 | B8b | 3-pyridyl | (CH₃)₂N—CH₂— | 3-CF₃-4-methylphenyl | |
| 96 | B2d-2 | 3-pyridyl | CN | 2-CF₃-4-methyl-1-F-phenyl | |
| 97 | B1a | 5-methyl-imidazo[2,1-b]thiazole | F | 2-CH₃-4-methyl-1-F-phenyl | |
| 98 | B1a | 3-pyridyl | F | 2-CF₃-4-methyl-1-OCH₃-phenyl | |
| 99 | B1b | 3-pyridyl | Br | 2-CF₃-4-methyl-1-F-phenyl | |
| 100 | B9 | 3-pyridyl | morpholino-CH₂— | 2-CF₃-4-methyl-1-F-phenyl | |
| 101 | B9 | 3-pyridyl | HO—CH₂— | 2-CF₃-4-methyl-1-F-phenyl | |

Table 2 lists both the experimental (column heading "Exper") and theoretical (column heading "Theor") elemental analysis values for carbon (C), hydrogen (H) and nitrogen (N) for compounds as prepared in the experimental part hereinabove.

TABLE 2

| Co. No. | C | | H | | N | |
|---|---|---|---|---|---|---|
| | Theor | Exper | Theor | Exper | Theor | Exper |
| 62 | 46.17 | 45.80 | 3.15 | 2.83 | 10.09 | 9.85 |
| 4 | 46.87 | 47.32 | 2.10 | 2.05 | 14.58 | 14.31 |
| 1 | 53.10 | 53.16 | 2.67 | 2.54 | 12.38 | 12.18 |
| 30 | 63.14 | 62.98 | 4.24 | 4.03 | 14.73 | 14.54 |
| 27 | 50.42 | 50.72 | 2.26 | 1.94 | 11.76 | 11.69 |

TABLE 2-continued

| Co. No. | C | | H | | N | |
|---|---|---|---|---|---|---|
| | Theor | Exper | Theor | Exper | Theor | Exper |
| 3 | 42.96 | 43.75 | 2.97 | 2.68 | 11.79 | 11.96 |
| 20 | 59.91 | 59.45 | 3.84 | 3.72 | 16.44 | 16.29 |
| 25 | 53.97 | 53.19 | 2.66 | 2.68 | 14.81 | 14.28 |

NMR Spectra Interpretation for Compounds 46 and 100.

Compound 46: $^1$H NMR (360 MHz; DMSO-d6) d ppm 2.57 (s, 1H) 7.30 (d, J=7.68 Hz, 1H) 7.56 (t, J=7.96 Hz, 1H) 7.92 (d, J=9.51 Hz, 1H) 8.15 (m, 2H) 8.82 (dt, J=8.37, 1.58 Hz, 1H) 8.89 (d, J=4.94 Hz, 1H) 9.15 (d, J=1.92 Hz, 1H) 10.73 (s, 1H).

Compound 100: $^1$H NMR (360 MHz; DMSO-d6) d ppm 2.45 (m, 4H) 3.59 (t, J=4.30 Hz, 4H) 3.72 (s, 2H) 7.49 (t, J=9.40 Hz, 1H) 7.52 (ddd, J=7.89, 4.83, 0.82 Hz, 1H) 7.90 (dt, J=8.76, 3.58 Hz, 1H) 8.05 (dt, J=7.91, 1.94 Hz, 1H) 8.29 (dd, J=6.36, 2.79 Hz, 1H) 8.58 (dd, J=4.76, 1.65 Hz, 1H) 8.89 (d, J=1.56 Hz, 1H) 10.59 (s, 1H).

C. Pharmacological Example

Example C.1

In Vitro Inhibition of TNF-α Production in Human Blood

Human Whole Blood Stimulation

Peripheral blood from healthy male donors was drawn into heparinized syringes (12.5 U heparin/ml). Blood samples were three-fold diluted in RMPI 1640 medium (Life Technologies, Belgium) supplemented with 2 mM L-glutamine, 100 U/ml penicillin and 100 μg/ml streptomycin, and 300 μl fractions were distributed in 24-well multidisc plates (Nunc, Roskilde, Denmark). Blood samples were preincubated (60 minutes at 37° C.) in a humidified 6% $CO_2$-atmosphere with 100 μl of drug solvent (final concentration 0.02% dimethylsulfoxide in RPMI 1640) or with 100 μl of an appropriate dose of test compound before being stimulated by the addition of 100 μl of lipopolysaccharide at a final concentration of 100 ng/ml. After 6 hours, cell-free supernatant fluids were collected by centrifugation and stored at −20° C. until tested for the presence of TNF-α.

Example C.2

In Vitro Inhibition of IL-12p40 Production in Human Blood

Human Whole Blood Stimulation

Peripheral blood from healthy male donors was drawn into heparinized syringes (12.5 U heparin/ml). Blood samples were three-fold diluted in RMPI 1640 medium (Life Technologies, Belgium) supplemented with 2 mM L-glutamine, 100 U/ml penicillin and 100 μg/ml streptomycin, and 300 μl fractions were distributed in 24-well multidisc plates (Nunc, Roskilde, Denmark). Blood samples were preincubated (60 minutes at 37° C.) in a humidified 6% $CO_2$-atmosphere with 100 μl of drug solvent (final concentration 0.02% dimethylsulfoxide in RPMI 1640) or with 100 μl of an appropriate dose of test compound before being stimulated by the addition of 100 μl of lipopolysaccharide at a final concentration of 100 ng/ml. After 24 hours, cell-free supernatant fluids were collected by centrifugation and stored at −20° C. until tested for the presence of IL-12p40.

Example C.3

Cytokine Measurements

Cytokine protein concentrations were determined by sandwich ELISA as described in Van Wauwe et al. (1996, Inflamm Res, 45, 357-363). Murine monoclonals used as capture antibodies to human cytokines were obtained from R&D Systems (Abingdon, United Kingdom) and code named MAB210 and MAB611 for TNF-α and IL-12 respectively. Biotinylated goat polyclonal antibodies used to detect human cytokines were from R&D Systems (BAF210, BAF219). Cytokine levels were calculated from standard curves using recombinant cytokines supplied by R&D Systems.

Table 3 lists the percentage inhibition of TNF-α and IL-12 production (column "% inh") at a test dose of $1\times10^{-6}$ and $1\times10^{-7}$ M for the compounds of the present invention.

TABLE 3

| Comp. No | % inhib. TNF-α | | % inhib. IL-12 (p40) | |
| --- | --- | --- | --- | --- |
| | $1\times10^{-6}$M | $1\times10^{-7}$M | $1\times10^{-6}$M | $1\times10^{-7}$M |
| 1 | 60 | 58 | 54 | 56 |
| 25 | 53 | 49 | 58 | 58 |
| 62 | 49 | 46 | 53 | 53 |
| 75 | | | 56 | 52 |
| 32 | | | 51 | |
| 14 | | | 52 | |
| 4 | | | 57 | |
| 27 | | | 58 | |
| 3 | | | 49 | |
| 20 | | | 51 | |
| 46 | | | 44 | |
| 23 | | | 48 | |

The invention claimed is:
1. A compound of formula

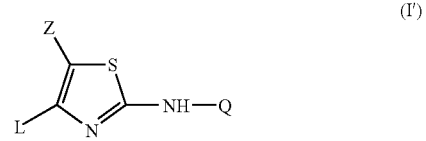

(I')

a N-oxide, a pharmaceutically acceptable addition salt, a quaternary amine and a stereochemically isomeric form thereof,
wherein
L is imidazothiazolyl;
Q is $C_{3-6}$cycloalkyl, phenyl, pyridyl, pyrimidinyl, pyrazinyl, pyridazinyl, benzthiazolyl, benzoxazolyl, benzimidazolyl, indazolyl, or imidazopyridyl, each of said rings optionally being substituted with up to three substituents each independently selected from halo; hydroxy; cyano; carboxyl; azido; amino; mono- or di($C_{1-6}$alkyl)amino; $C_{1-6}$alkylcarbonylamino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino or mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo-$C_{1-6}$alkyloxy; polyhalo$C_{1-6}$alkylcarbonyl; piperidinylamino; 1-methyl-4-piperidinylamino; morpholinyl, $C_{1-4}$alkyl-S(=O)$_n$— or $H_2N$—S(=O)$_n$—; and n is an integer of 1 or 2;
or
Q is a radical of formula

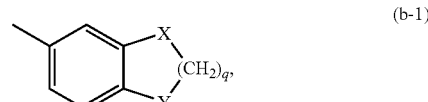

(b-1)

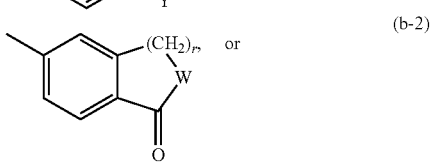

(b-2)

or

-continued

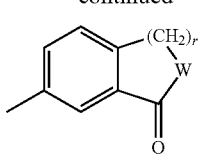
(b-3)

and wherein r is an integer from 1 to 3; q is an integer from 1 to 4;

X and Y are each independently O, $NR^3$, $CH_2$ or S, with $R^3$ being hydrogen or $C_{1-4}$alkyl;

W is O or $NR^4$, with $R^4$ being hydrogen or $C_{1-4}$ alkyl;

and wherein aryl is phenyl, optionally substituted with up to five substituents each independently selected from halo, hydroxy, $C_{1-6}$alkyl, polyhalo$C_{1-6}$alkyl, $C_{1-6}$alkyloxy, $C_{1-6}$alkylthio, cyano, nitro, amino or mono- or di($C_{1-6}$alkyl)amino;

and

Z is halo; $C_{1-6}$alkyl; $C_{1-6}$alkyl substituted with amino; $C_{1-6}$alkyl substituted with hydroxy; 4-piperidinylaminomethyl; or 1-methyl-4-piperidinylaminomethyl.

2. A compound according to claim 1 wherein Q is benzthiazolyl; pyridyl substituted with halo or $C_{1-6}$alkyl; phenyl or phenyl substituted with one, two or three substituents selected from halo, $C_{1-6}$alkyl, polyhalo$C_{1-6}$alkyl, $C_{1-6}$alkyloxycarbonyl, hydroxy, $C_{1-6}$alkyloxy, $C_{1-6}$alkylthio, 1-methyl-2-imidazolyl; Z is halo; cyano; $C_{1-6}$alkylcarbonyl; aminocarbonyl; $C_{1-6}$alkyloxycarbonyl; $C_{1-6}$alkyl; $C_{1-6}$alkyl substituted with hydroxy, $C_{1-6}$alkyloxy, amino, mono- or di($C_{1-6}$alkyl)amino, piperidinylamino, 1-methyl-4-piperidinylamino or morpholinyl.

3. A pharmaceutical composition comprising a pharmaceutically acceptable carrier and as active ingredient a therapeutically effective amount of a compound as claimed in claim 1.

4. A pharmaceutical composition comprising a compound as defined in claim 1, and another anti-inflammatory or immunosuppressive compound.

5. The compound of claim 1 which is 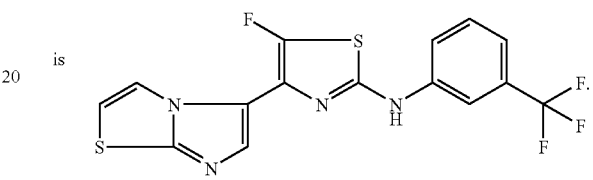

* * * * *